US012226427B2

(12) United States Patent
Benvenisty et al.

(10) Patent No.: US 12,226,427 B2
(45) Date of Patent: Feb. 18, 2025

(54) TREATMENT FOR GENE REACTIVATION

(71) Applicant: YISSUM RESEARCH DEVELOPMENT COMPANY OF THE HEBREW UNIVERSITY OF JERUSALEM LTD., Jerusalem (IL)

(72) Inventors: Nissim Benvenisty, Jerusalem (IL); Dan Vershkov, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 925 days.

(21) Appl. No.: 17/268,655

(22) PCT Filed: Aug. 15, 2019

(86) PCT No.: PCT/IL2019/050917
§ 371 (c)(1),
(2) Date: Feb. 16, 2021

(87) PCT Pub. No.: WO2020/035866
PCT Pub. Date: Feb. 20, 2020

(65) Prior Publication Data
US 2021/0169908 A1 Jun. 10, 2021

Related U.S. Application Data

(60) Provisional application No. 62/719,060, filed on Aug. 16, 2018.

(51) Int. Cl.
*A61K 31/706* (2006.01)
*A61K 31/437* (2006.01)
*A61P 25/00* (2006.01)

(52) U.S. Cl.
CPC .......... *A61K 31/706* (2013.01); *A61K 31/437* (2013.01); *A61P 25/00* (2018.01)

(58) Field of Classification Search
None
See application file for complete search history.

(56) References Cited

U.S. PATENT DOCUMENTS

2005/0130151 A1* 6/2005 Warren ................ C12Q 1/6883
435/325
2018/0256749 A1* 9/2018 Green ................ A61K 39/3955

FOREIGN PATENT DOCUMENTS

WO WO-2015168149 A2 * 11/2015 ........... A61K 31/137
WO 2017049192 A1 3/2017

OTHER PUBLICATIONS

Wilkinson, G. Pharmacokinetics, The Dynamics of Drug Absorption, Distribution, and Elimination (2001). In: Goodman and Gilman's the pharmacological basis of therapeutics. International edition, 10th edition, Mc Grow Hill, 971. (Year: 2001).*
Momparler RL, CôtéS, Momparler LF, Idaghdour Y. Inhibition of DNA and Histone Methylation by 5-Aza-2'-Deoxycytidine (Decitabine) and 3-Deazaneplanocin-A on Antineoplastic Action and Gene Expression in Myeloid Leukemic Cells. Front Oncol. Feb. 15, 2017;7:19. doi: 10.3389/fonc.2017.00019. PMID: 28261562; PMCID: PMC5309231.
Diaz Perez, S. V., Kim, R., Li, Z., Marquez, V. E., Patel, S., Plath, K., & Clark, A. T. (2012). Derivation of new human embryonic stem cell lines reveals rapid epigenetic progression in vitro that can be prevented by chemical modification of chromatin. Human molecular genetics, 21(4), 751-764. https://doi.org/10.1093/hmg/ddr506.
Cheung, A. Y., Horvath, L. M., Carrel, L., & Ellis, J. (2012). X-chromosome inactivation in rett syndrome human Induced pluripotent stem cells. Frontiers in psychiatry, 3, 24. https://doi.org/10.3389/fpsyt.2012.00024.
Kumari D, Usdin K. Polycomb group complexes are recruited to reactivated FMR1 alleles in Fragile X syndrome in response to FMR1 transcription. Hum Mol Genet. Dec. 15, 2014;23(24):6575-83. doi: 10.1093/hmg/ddu378. Epub Jul. 23, 2014. PMID: 25055869; PMCID: PMC4240206.
Rovozzo R, Korza G, Baker MW, Li M, Bhattacharyya A, Barbarese E, et al. (2016) CGG Repeats in the 5'UTR of FMR1 RNA Regulate Translation of Other RNAs Localized in the Same RNA Granules. PLoS ONE 11(12): e0168204. doi:10.1371/journal.pone.0168204.
Sun F, Chan E, Wu Z, Yang X, Marquez VE, Yu Q. Combinatorial pharmacologic approaches target EZH2-mediated gene repression in breast cancer cells. Mol Cancer Ther. Dec. 2009;8(12):3191-202. doi: 10.1158/1535-7163. MCT-09-0479. PMID: 19934278; PMCID: PMC2794891.
Vershkov D, Fainstein N, Suissa S, Golan-Lev T, Ben-Hur T, Benvenisty N. FMR1 Reactivating Treatments in Fragile X iPSC-Derived Neural Progenitors In Vitro and In Vivo. Cell Rep. Mar. 5, 2019;26(10):2531-2539.e4. doi: 10.1016/j.celrep.2019.02.026. PMID: 30840878.
Urbach A, Bar-Nur O, Daley GQ, Benvenisty N. Differential modeling of fragile X syndrome by human embryonic stem cells and induced pluripotent stem cells. Cell Stem Cell. May 7, 2010;6(5):407-11. doi: 10.1016/j.stem.2010.04.005. PMID: 20452313; PMCID: PMC3354574.
Weissbein U, Plotnik O, Vershkov D, Benvenisty N. Culture-induced recurrent epigenetic aberrations in human pluripotent stem cells. PLoS Genet. Aug. 24, 2017;13(8):e1006979. doi: 10.1371/journal.pgen.1006979. PMID: 28837588; PMCID: PMC5587343.
Bar-Nur O, Caspi I, Benvenisty N. Molecular analysis of FMR1 reactivation in fragile-X induced pluripotent stem cells and their neuronal derivatives. J Mol Cell Biol. Jun. 2012;4(3):180-3. doi: 10.1093/jmcb/mjs007. Epub Mar. 19, 2012. PMID: 22430918.

(Continued)

*Primary Examiner* — Dale R Miller
(74) *Attorney, Agent, or Firm* — The Roy Gross Law Firm, LLC; Roy Gross

(57) ABSTRACT

Methods of reactivating transcription of a fragile X mental retardation 1 (FMR1) gene and treating FMR1-associated diseases are provided. Compositions and kits for doing same are also provided.

19 Claims, 26 Drawing Sheets
(11 of 26 Drawing Sheet(s) Filed in Color)
Specification includes a Sequence Listing.

(56) References Cited

OTHER PUBLICATIONS

Brouwer JR, Mientjes EJ, Bakker CE, Nieuwenhuizen IM, Severijnen LA, Van der Linde HC, Nelson DL, Oostra BA, Willemsen R. Elevated Fmr1 mRNA levels and reduced protein expression in a mouse model with an unmethylated Fragile X full mutation. Exp Cell Res. Jan. 15, 2007;313(2):244-53. doi: 10.1016/j.yexcr.2006.10.002. Epub Oct. 13, 2006. PMID: 17150213; PMCID: PMC1852528.
Chiurazzi P, Pomponi MG, Willemsen R, Oostra BA, Neri G. In vitro reactivation of the FMR1 gene involved in fragile X syndrome. Hum Mol Genet. Jan. 1998;7(1):109-13. doi: 10.1093/hmg/7.1.109. PMID: 9384610.
Coffee B, Keith K, Albizua I, Malone T, Mowrey J, Sherman SL, Warren ST. Incidence of fragile X syndrome by newborn screening for methylated FMR1 DNA. Am J Hum Genet. Oct. 2009;85(4):503-14. doi: 10.1016/j.ajhg.2009.09.007. PMID: 19804849; PMCID: PMC2756550.
Colak D, Zaninovic N, Cohen MS, Rosenwaks Z, Yang WY, Gerhardt J, Disney MD, Jaffrey SR. Promoter-bound trinucleotide repeat mRNA drives epigenetic silencing in fragile X syndrome. Science. Feb. 28, 2014;343(6174):1002-5. doi: 10.1126/science.1245831. PMID: 24578575; PMCID: PMC4357282.
Eiges R, Urbach A, Malcov M, Frumkin T, Schwartz T, Amit A, Yaron Y, Eden A, Yanuka O, Benvenisty N, Ben-Yosef D. Developmental study of fragile X syndrome using human embryonic stem cells derived from preimplantation genetically diagnosed embryos. Cell Stem Cell. Nov. 2007;1(5):568-77. doi: 10.1016/j.stem.2007.09.001. PMID: 18371394.
Gholizadeh S, Arsenault J, Xuan IC, Pacey LK, Hampson DR. Reduced phenotypic severity following adeno-associated virus-mediated Fmr1 gene delivery in fragile X mice. Neuropsychopharmacology. Dec. 2014;39 (13):3100-11. doi: 10.1038/npp.2014.167. Epub Jul. 7, 2014. PMID: 24998620; PMCID: PMC4229583.
Ghoshal K, Datta J, Majumder S, Bai S, Kutay H, Motiwala T, Jacob ST. 5-Aza-deoxycytidine induces selective degradation of DNA methyltransferase 1 by a proteasomal pathway that requires the KEN box, bromo-adjacent homology domain, and nuclear localization signal. Mol Cell Biol. Jun. 2005;25(11):4727-41. doi: 10.1128/MCB.25.11.4727-4741.2005. Erratum in: Mol Cell Biol. Apr. 30, 2018;38(10 ): PMID: 15899874; PMCID: PMC1140649.
Park CY, Halevy T, Lee DR, Sung JJ, Lee JS, Yanuka O, Benvenisty N, Kim DW. Reversion of FMR1 Methylation and Silencing by Editing the Triplet Repeats in Fragile X iPSC-Derived Neurons. Cell Rep. Oct. 13, 2015;13(2):234-41. doi: 10.1016/j.celrep.2015.08.084. Epub Oct. 1, 2015. PMID: 26440889.
Patel K, Dickson J, Din S, Macleod K, Jodrell D, Ramsahoye B. Targeting of 5-aza-2'-deoxycytidine residues by chromatin-associated DNMT1 induces proteasomal degradation of the free enzyme. Nucleic Acids Res. Jul. 2010;38(13):4313-24. doi: 10.1093/nar/gkq187. Epub Mar. 25, 2010. PMID: 20348135; PMCID: PMC2910061.
PCT International Search Report for International Application No. PCT/IL2019/050917, mailed May 12, 2019, 5pp.
PCT Written Opinion for International Application No. PCT/IL2019/050917, mailed May 12, 2019, 6pp.
PCT International Preliminary Report on Patentability for International Application No. PCT/IL2019/050917, issued Feb. 16, 2021, 7pp.

* cited by examiner

SEQUENCE LISTING

<160> NUMBER OF SEQ ID NOS: 7

<210> SEQ ID NO 1
<211> LENGTH: 22
<212> TYPE: DNA
<213> ORGANISM: Homo sapiens

<400> SEQUENCE: 1
gcagcatgtg atgcaactta ca                                              22

<210> SEQ ID NO 2
<211> LENGTH: 19
<212> TYPE: DNA
<213> ORGANISM: Homo sapiens

<400> SEQUENCE: 2
cgcctctttg gcacacatt                                                  19

<210> SEQ ID NO 3
<211> LENGTH: 20
<212> TYPE: DNA
<213> ORGANISM: Homo sapiens

<400> SEQUENCE: 3
agccacatcg ctcagacacc                                                 20

<210> SEQ ID NO 4
<211> LENGTH: 19
<212> TYPE: DNA
<213> ORGANISM: Homo sapiens

<400> SEQUENCE: 4
gtactcagcg ccagcatcg                                                  19

```
<210> SEQ ID NO 5
<211> LENGTH: 20
<212> TYPE: DNA
<213> ORGANISM: Artificial
<220> FEATURE:
<223> OTHER INFORMATION: Synthetic

<400> SEQUENCE: 5
gaggccagaa ggaggaaccg                                              20

<210> SEQ ID NO 6
<211> LENGTH: 20
<212> TYPE: DNA
<213> ORGANISM: Homo sapiens

<400> SEQUENCE: 6
gatcccagtc ccgagtatgc                                              20

<210> SEQ ID NO 7
<211> LENGTH: 20
<212> TYPE: DNA
<213> ORGANISM: Homo sapiens

<400> SEQUENCE: 7
gaggccagaa ggaggaaccg                                              20
```

TREATMENT FOR GENE REACTIVATION

CROSS REFERENCE TO RELATED APPLICATIONS

This application is a National Phase of PCT Patent Application No. PCT/IL2019/050917 having International filing date of Aug. 15, 2019, which claims the benefit of priority of U.S. Provisional Patent Application No. 62/719,060, filed Aug. 16, 2018. The contents of the above applications are all incorporated by reference as if fully set forth herein in their entirety.

FIELD OF INVENTION

The present invention is in the field of gene reactivation and Fragile X Syndrome treatment.

BACKGROUND OF THE INVENTION

Fragile X syndrome (FXS), the most prevalent hereditary form of intellectual impairment, is mainly caused by the expansion of a repetitive CGG sequence in the 5'-untranslated region (UTR) of the Fragile X mental retardation 1 (FMR1) gene, located on the X chromosome. When the expansion size exceeds 200 repeats, it leads to the epigenetic inactivation of FMR1 and the loss of its protein product, FMRP. The fully expanded FMR1 locus is characterized by DNA hypermethylation, local gain of repressive histone marks and the loss of euchromatic histone marks. Although FMR1 knock-out animal models were useful in characterizing the cellular roles of FMRP, knock-in mouse models carrying an expanded CGG tract failed to recapitulate the loss of FMR1 transcription, thus precluding the study of expansion mediated FMR1 inactivation in vivo.

The establishment of human pluripotent stem cell (PSC) models for FXS provided an inexhaustible source of human cells carrying FXS-causing mutations. Characterization of induced pluripotent stem cells (iPSCs) derived from FXS patients revealed DNA hypermethylation of the expanded FMR1 allele, as well as a complete silencing of FMR1 expression, thus allowing their use for the study of FMR1 inactivation. Recently, CRISPR/Cas9-based correction of FXS-iPSCs has yielded genetically edited patient-derived cell lines, which show restoration of FMRP expression, and present an isogenic control for investigating the disease phenotype.

The existence of rare individuals of apparent normal intelligence that harbor an unmethylated full CGG expansion suggests that targeting the transcriptional inactivation of FMR1 can serve as a therapeutic strategy for FXS. Pharmacological demethylation by the DNA methyltransferase (DNMT) inhibitor 5-azacytidine was able to restore FMR1 expression in FXS-iPSCs and their neural derivatives (Bar-Nur et al., 2012). However, the long-term consequences of the treatment, as well as its genome-wide effects, were not assessed in neural cells. In addition, it is yet to be established whether there are additional epigenetic processes that are involved in the maintenance of FMR1 inactivation, that could be targeted in order to induce FMR1 transcription in affected cells. Improved methods of reactivating the FMR1 genes, with minimal side effects and a long-lasting effect are greatly needed.

SUMMARY OF THE INVENTION

The present invention provides methods of reactivating transcription of a fragile X mental retardation 1 (FMR1) gene and treating FMR1-associated diseases by administering a combination of 5-aza-2-deoxycytidine (5-azadC) and 3-Deazaneoplanocin A (DZNep). Methods of treating Fragile X Syndrome (FXS) by administering DZNep alone or in combination with 5-azadC are also provided.

According to a first aspect, there is provided a method of reactivating transcription of a fragile X mental retardation 1 (FMR1) gene in a cell, comprising contacting the cell with 5-aza-2-deoxycytidine (5-azadC) and 3-Deazaneoplanocin A (DZNep), thereby reactivating transcription of the FMR1 gene in the cell.

According to another aspect, there is provided a method of treating an FMR1-associated disease in a subject in need thereof, the method comprising administering to the subject a treatment, the treatment selected from the group consisting of 3-Deazaneoplanocin A (DZNep), and DZNep in combination with 5-aza-2-deoxycytidine (5-azadC), thereby treating an FMR1-associated disease in a subject.

According to another aspect, there is provide a pharmaceutical composition comprising 5-aza-2-deoxycytidine (5-azadC) and 3-Deazaneoplanocin A (DZNep) for use in reactivating transcription of a fragile X mental retardation 1 (FMR1) gene in a cell.

According to another aspect, there is provided a pharmaceutical composition comprising a treatment, wherein the treatment is selected from the group consisting of. 3-Deazaneoplanocin A (DZNep), and DZNep in combination with 5-aza-2-deoxycytidine (5-azadC) for use in treating a FMR1-associated disease in a subject in need thereof.

According to another aspect, there is provided a kit comprising 5-aza-2-deoxycytidine (5-azadC) and 3-Deazaneoplanocin A (DZNep).

According to some embodiments, the cell or a cell from the subject comprises an expansion of a repetitive CGG sequence in a 5' UTR of a FMR1 gene.

According to some embodiments, the expansion comprises at least 55 CGG repeats.

According to some embodiments, the expansion comprises at least 200 repeats.

According to some embodiments, the cell or a cell from the subject is a neuronal cell.

According to some embodiments, the neuronal cell is from a region of the brain selected from hippocampus, temporal cortices, visual cortex, cerebral cortex, amygdala, caudate nucleus, and temporal gyrus.

According to some embodiments, the neuronal cell is located in the hippocampus.

According to some embodiments, the 5-azadC and DZNep are contacted or administered simultaneously or sequentially.

According to some embodiments, the 5-azadC and DZNep are contacted or administered simultaneously.

According to some embodiments, the 5-azadC and DZNep are contacted or administered less than 3 days apart.

According to some embodiments, the treating comprises reactivation of transcription of FMR1.

According to some embodiments, the reactivating persists for longer than 30 days.

According to some embodiments, the reactivating comprises increased expression of FMR1 as compared to reactivation with 5-azadC alone, and wherein the increase occurs within 3 days of the contacting or administering.

According to some embodiments, the increased expression comprises an increase of at least 30% by 4 days after the contacting or administering.

According to some embodiments, the administering comprises intravenous, intracranial, or intrathecal administration.

According to some embodiments, the administering comprises a 5-azadC dosage of between 0.1 and 2 mg/kg/day.

According to some embodiments, the FMR1-associated disease is selected from Fragile X Syndrome (FXS), schizophrenia, bipolar disorder, psychotic bipolar disorder, dementia, fragile X-associated tremor/ataxia syndrome (FXTAS), and FMR1-related primary ovarian insufficiency (POI), Angelman syndrome, Prader-Willi Syndrome, Beckwith-Wiedemann syndrome, Silver-Russell syndrome, lupus, rheumatoid arthritis, multiple sclerosis, diabetes and alcoholism.

According to some embodiments, the FMR1-associated disease is FXS.

According to some embodiments, the 5-azadC comprises a label stating the 5-azadC is for use in combination with the DZNep, the DZNep comprises a label stating the DZNep is for use in combination with the 5-azadC or both.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
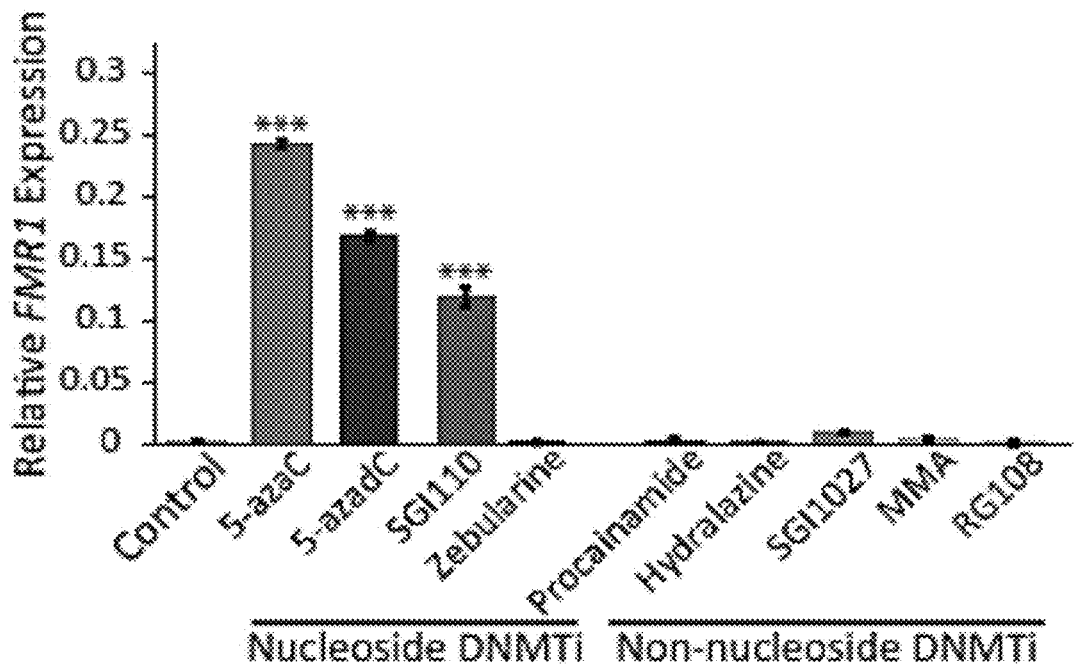
FIGS. 1A-M: Screening for FMR1 Reactivating Compounds. (1A) A bar graph of RT-PCR analysis of FMR1 transcript levels in FXS-iPSCs B #40 following 96-hour treatment with the nucleoside DNMT inhibitors: 5-azacytidine (5-azaC, 5 μM), 5-aza-2-deoxycytidine (5-azadC, 5 μM), SGI-110 (Guadecitabine, 2 μM), Zebularine (100 μM), and the non-nucleoside DNMT inhibitors: Procainamide (100 μM), Hydralazine (100 μM), SGI-1027 (5 μM), Mythramycin A (MMA) (10 μM), RG108 (20 μM). (1B) A diagram of FMR1 reactivation screening workflow. FXS-iPSCs A #52 were seeded in 96-well plates. A total of 140 epigenetic modifiers were screened at two concentrations (2 μM, 20 μM) and three replicates. After 72-hour incubation, the cells were immunostained for FMRP. Automated image acquisition and analysis were used to assess the percent of FMRP expressing cells. (1C) Micrographs of immunofluorescence staining of FMRP (red) in WT-ESCs and FXS-iPSCs A #52. Nuclear staining is in blue (DAPI). (1D) A bar graph of FMRP expression in different ratios of WT and FXS-iPSC culture. FXS-iPSCs and WT-ESCs were mixed at different ratios and seeded in a 96-well plate. Immunostaining was performed following 24-hour incubation. Automated image acquisition and analysis were used to detect the fraction of FMRP expressing cells. (1E) A bar graph showing the average fraction of FMRP positive cells following different incubation times with 5-aza-2-deoxycytidine (1 μM), relative to WT-ESCs. Each well was evaluated for the number of FMRP expressing cells. (1F) Scatterplot analysis (of a representative plate of 7 plates) of FMRP reactivation screen. Each compound was evaluated for cell survival following the treatment versus the fraction of FMRP expressing cells. Some compounds (red square) were too toxic to assess using our system. Others (purple square) did not induce a significant FMRP signal. Compounds that induced FMRP expression (orange square) were further tested using RT-PCR. (1G-H) Bar graphs of RT-PCR analysis of FMR1 transcript levels. (1G) Analysis following 96-hour treatment of FXS-iPSCs A #52 with either DZNep (20 uM), or 5-azadC (1 uM). (1H) DZNep potentiates the effect of demethylating treatment compared with DNMT inhibitors alone. Two FXS-iPSC cell lines were treated for 4 days with DMSO only, 5-azadC (100 nM) and DMSO, or 5-azadC and DZNep (25 uM). (1I) A bar graph showing RT-PCR analysis of FMR1 mRNA expression in FXS-C #2 iPSCs, treated by 50 nM 5-azadC for 4 or 5 days. (1J) A bar chart showing RT-PCR analysis of FMR1 mRNA expression in FXS-A #52 iPSCs, treated by different 5-azadC concentrations for 3 days. (1K) A bar graph showing the relative FMR1 expression induced by 5-azadc alone, or with HATs GSK126 (25 uM), or DZNEP. (1L) A bar chart showing relative wild-type transcript levels (analysed by qRT-PCR) of the targeted DNMT1 gene in FXS-iPSCs 3 days after the delivery of sgRNA and Cas9. Control lines received only Cas9 in the absence of a sgRNA. Values represent the averages of two biological replicate experiments with three technical replicates for each. (1M) A bar chart showing changes in FMR1 expression levels in FXS-iPSCs after DNMT1 disruption, as detected by RT-PCR. $*p<0.05$, $***p<0.001$. Error bars represent SEM.

The present invention, in some embodiments, provides methods of reactivating transcription of a fragile X mental retardation 1 (FMR1) gene in a cell and treating an FMR1-associated disease in a subject. The method comprises administering a combination of 5-aza-2-deoxycytidine (5-azadC) and 3-Deazaneoplanocin A (DZNep) to the cell or subject. Methods of treating Fragile X Syndrome (FXS) comprising administering DZNep alone or in combination with 5-azadC are also provided.

The invention is based, at least in part, on the surprising finding that when administered together 5-azadC and DZNep had a synergistic effect on reactivating FMR1 transcription. The strong synergistic combination was not observed when other histone methyltransferase (HMT) inhibitors, even those that target EZH2 as well. Further, unlike some other HMTs DZNep treatment alone resulted in modest decrease in DNA methylation levels in the FMR1 promoter, suggesting that the targeting of inhibitory histone modifications can affect the maintenance of DNA hypermethylation in the FMR1 promoter. Further, the inventors found that the increase in FMR1 transcription occurred immediately upon treatment, and that the reactivation of FMR1 expression persisted without re-silencing of FMR1 and with minimal or no cell death.

By a first aspect, there is provided a method of reactivating transcription of a silenced genetic locus in a cell, comprising contacting the cell with a treatment, wherein the treatment is selected from the group consisting of: 3-Deazaneoplanocin A (DZNep), and DZNep in combination with 5-aza-2-deoxycytidine (5-azadC), thereby reactivating transcription of a silenced genetic locus in the cell.

By another aspect, there is provided a method of treating a disease or condition characterized by silenced transcription of at least one genetic locus in a subject in need thereof, comprising contacting the cell with a treatment, wherein the treatment is selected from the group consisting of: 3-Deazaneoplanocin A (DZNep), and DZNep in combination with 5-aza-2-deoxycytidine (5-azadC), thereby treating the disease.

By another aspect, there is provided a method of reducing the dose of 5-azadC administered to a subject in need thereof, the method comprising co-administering DZNep with the 5-azadC.

By another aspect, there is provided a pharmaceutical composition comprising a treatment, wherein the treatment is selected from the group consisting of: 3-Deazaneoplanocin A (DZNep), and 5-aza-2-deoxycytidine (5-azadC) in combination with DZNep.

By another aspect, there is provided a kit comprising 5-aza-2-deoxycytidine (5-azadC), 3-Deazaneoplanocin A (DZNep) or both.

In some embodiments, the treatment is DZNep. In some embodiments, the treatment is 5-azadC and DZNep. In some embodiments, the treatment is DZNep in combination with 5-azadC. In some embodiments, the treatment is DZNep alone.

As used herein, the phrase "genetic locus" refers to a fixed position or region in the genome. In some embodiments, the genetic locus is a region that codes for an RNA transcript. In some embodiments, the genetic locus can be transcribed. In some embodiments, the genetic locus comprises a sequence of a gene, or a non-coding RNA. The non-coding RNA is a regulatory RNA. In some embodiments, the regulatory RNA is selected from a mircroRNA (miR), a long non-coding RNA, a rRNA and a tRNA.

In some embodiments, the genetic locus does not comprise a silenced tumor suppressor gene. In some embodiments, the genetic locus does not comprise a proapoptotic gene. In some embodiments, the genetic locus comprises an imprinted gene. In some embodiments, the genetic locus comprises FMR1. In some embodiments, the genetic locus is FMR1. In some embodiments, genetic locus comprises a neuronal gene or non-coding RNA. In some embodiments, the genetic locus comprises a neuron specific gene or non-coding RNA. In some embodiments, the genetic locus comprises a non-hematological gene or non-coding RNA.

As such, a "silenced" genetic locus is a region of the genome that can be transcribed, but in which transcription has been shut off. Thus, a silenced locus is not merely lacking binding of a transcription factor, polymerase or other activator to start transcription, but rather is actively shut off. In some embodiments, a silenced locus comprises heterochromatin. In some embodiments, a silenced locus comprises a heterochromatic promoter. In some embodiments, a silenced locus comprises silencing DNA methylation. In some embodiments, a silenced locus comprises silencing DNA methylation in the promoter of a gene in the locus. In some embodiments, a silenced locus comprises silencing histone modification. In some embodiments, the silencing histone modification are in the promotor of a gene in the locus. Examples of silencing histone modification include but are not limited to Histone H3 lysine 9 (H3K9) di- and tri-methylation, H3K27 trimethylation and H4K20 trimethylation. In some embodiments, the silenced locus comprises H3K27 trimethylation.

In some embodiments, the silenced locus comprises DNA and histone methylation. In some embodiments, the silenced locus comprises DNA methylation and H3K27 trimethylation.

In some embodiments, reactivating transcription comprises production of RNA from the locus. In some embodiments, reactivating transcription comprises production of RNA from the locus, when no previous RNA was produced. In some embodiments, the reactivation is reactivation of transcription of a particular RNA from the locus. A skilled artisan will appreciate that a particular genomic location may transcribe several distinct RNA transcripts, and only one or a portion of those transcripts may be silenced while other transcripts are transcribed. Thus, reactivating may comprise reactivation of a specific transcript from the locus even if other transcripts are not reactivated, and/or were never silenced. In some embodiments, the reactivation is reactivation of transcription of a silenced RNA.

In some embodiments, the reactivating comprises an increased expression of the silenced transcript as compared to reactivation with 5'azadC alone. In some embodiments, the reactivating comprises an increased expression of the silenced transcript as compared to reactivation with 5'-azacytidine (5' azaC) alone. In some embodiments, the reactivating comprises an increased expression of the silenced transcript as compared to reactivation with 5' azadC and a non-DZNep HAT. In some embodiments, the non-DZNep HAT is selected from GSK126, GSK343 and UNC1999. In some embodiments, the non-DZNep HAT is UNC1999. In some embodiments, the non-DZNep HAT is GSK126. In some embodiments, the non-DZNep HAT is selected from GSK126 and UNC1999.

In some embodiments, the reactivating begins immediately after the contacting or administering. In some embodiments, the reactivating begins within 1 hour, 2 hours, 4 hours, 6 hours, 8 hours, 12 hours, 18 hours, 24 hours, 48 hours or 72 hours after the contacting or administering. Each possibility represents a separate embodiment of the invention. In some embodiments, the reactivating occurs within 3 days of the contacting or administering. In some embodiments, the increased expression as compared to a different treatment begins immediately after the contacting or administering. In some embodiments, the increased expression as compared to a different treatment begins within 1 hour, 2 hours, 4 hours, 6 hours, 8 hours, 12 hours, 18 hours, 24 hours, 48 hours or 72 hours after the contacting or administering. Each possibility represents a separate embodiment of the invention. In some embodiments, the increased expression as compared to a different treatment occurs within 3 days of the contacting or administering.

In some embodiments, the increased expression as compared to a different treatment comprises at least a 10%, 20%, 30%, 40%, 50%, 60%, 70%, 80%, 90%, or 100% increase in expression of the silenced transcript over the expression of the transcript after reactivation with the other treatment. Each possibility represents a separate embodiment of the invention. In some embodiments, the increased expression as compared to a different treatment is at least 30%. In some embodiments, the increased expression is at least 30% and occurs within 4 days after the contacting or administering. In some embodiments, the increased expression is at least 30% and occurs within 3 days after the contacting or administering.

In some embodiments, the reactivating persists for at least 10, 20, 25, 30, 35, 40, 45, or 50 days. Each possibility represents a separate embodiment of the invention. In some embodiments, the reactivating persists for at least 30 days. In some embodiments, the reactivating persists for longer than 10, 20, 25, 30, 35, 40, 45, or 50 days. Each possibility represents a separate embodiment of the invention. In some embodiments, the reactivating persists for longer than 30 days. In some embodiments, expression of the previously silenced transcript persists for at least or longer than 10, 20, 25, 30, 35, 40, 45, or 50 days. Each possibility represents a separate embodiment of the invention. In some embodiments, expression of the previously silenced transcript persists for at least or longer than 30 days.

In some embodiments, the cell is in vivo. In some embodiments, the cell is in a subject. In some embodiments, cell is in vitro. In some embodiments, cell is ex vivo and is administered to a subject after the contacting. In some embodiments, the cell is a eukaryotic cell. In some embodiments, the cell is a mammalian cell. In some embodiments, the cell is a human cell. In some embodiments the cell is from a female subject. In some embodiments, the cell is from a male subject. In some embodiments, the cell is from a subject with only one X chromosome. In some embodiments, the subject is heterozygous for CGG repeat expansion. In some embodiments, the subject is homozygous for CGG repeat expansion. In some embodiments, the cell is a diseased cell. In some embodiments, the cell is a neuronal cell. In some embodiments, the cell is not a cancerous cell. In some embodiments, the cell is not a hematological cell. In some embodiments, the neuronal cell is from a region of the brain effected by FXS. In some embodiments, the neuronal cell is from a region of the brain selected from the hippocampus, temporal cortices, visual cortex, cerebral cortex, amygdala, caudate nucleus, and temporal gyrus. In some embodiments, the cell is from the hippocampus. In some embodiments, the cell is a hippocampal cell.

In some embodiments, the cell comprises a silenced genetic locus. In some embodiments, the genetic locus is abnormally silenced. In some embodiments, the silencing of the locus is pathological. In some embodiments, the silencing of the locus is the cause of a pathology. In some embodiments, at most 1, 2, 3, 4, 5, 6, 7, 8, 9, or 10 genetic loci are silenced in the cell. Each possibility represents a separate embodiment of the invention. In some embodiments, at most 1, 2, 3, 4, 5, 6, 7, 8, 9, or 10 genetic loci are abnormally silenced in the cell. Each possibility represents a separate embodiment of the invention. As used herein, the term "abnormal" refers to a state that is different that the state in a comparable cell that does not suffer from a pathology. A skilled artisan will appreciate that a cell of a given type (neuron, cardiomyocyte, T cell, etc.) can be compared to another cell of the same type, or to many cells of the same type and if a particular gene's expression is grossly different, its expression can be considered abnormal. In some embodiments, abnormal silencing comprises at least a 50%, 60%, 70%, 80%, 90%, 95%, 97%, 99% or 100% reduction in transcription as compared to a healthy cell of the same cell type. Each possibility represents a separate embodiment of the invention. In some embodiments, only one genetic loci is abnormally silenced.

In some embodiments, the cell comprises abnormal imprinting. In some embodiments, the cell comprises an abnormally silenced X chromosome. In some embodiments, the cell does not comprise canonical X chromosome inactivation (XCI). In some embodiments, abnormal silencing is any X chromosome silencing that is not XCI. In some embodiments, the cell comprises silencing of the FMR1 gene. In some embodiments, the cell comprises abnormal silencing of the FMR1 gene. In some embodiments, the cell comprises an expansion of a repetitive CGG sequence. In some embodiments, the CGG sequence is in a 5' UTR. In some embodiments, the 5' UTR is the 5' UTR of the FMR1 gene. In some embodiments, the expansion the expansion comprises at least 55 CGG repeats. In some embodiments, the expansion comprises at least 50 CGG repeats. In some embodiments, the expansion comprises at least 200 repeats. In some embodiments, a cell with at least 50 or 55 repeats is a cell with a FMR1 permutation. In some embodiments, a subject comprising cells with at least 50 or 55 repeats suffers from FMR1 permutation condition. In some embodiments, a cell with at least 200 repeats is a cell with FXS. In some embodiments, a cell with between 50 or 55 repeats and 200 repeats is a cell with a FMR1 permutation.

In some embodiments, the subject is a mammal. In some embodiments, the subject is a human. In some embodiments, the subject is a fetus. In some embodiments, the subject is a child. In some embodiments, the subject is an adult. In some embodiments the subject is female. In some embodiments, the subject is male. In some embodiments, the subject has only 1 X chromosome per cell. In some embodiments, the subject is less than 1, 2, 3, 4, 5, 6, 7, 8, 9 or 10 years old. Each possibility represents a separate embodiment of the invention. In some embodiments, the administration occurs post-partum. In some embodiments, the administration occurs from 1 month, 3 months, 6 months, 9 months, 1 year, 2 years, or 3 years and on. In some embodiments, the subject is elderly. In some embodiments, the subject is older than 10, 15, 20, 30, 40, 50, 60, 70 or 80 years old. Each possibility represents a separate embodiment of the invention. In some embodiments, the administration is continued indefinitely. In some embodiments, the administration is continued for as long as symptoms of the condition persists. In some embodiments, the administration is for a set time, but is restarted if re-silencing of the genetic locus occurs.

In some embodiments, the disease is characterized by silenced transcription. In some embodiments, the disease characterized by silenced transcription is not cancer. In some embodiments, the disease is characterized by an expansion of a repetitive CGG sequence in a 5' UTR of a FMR1 gene. In some embodiments, the disease is a monoallelic disease. In some embodiments, the disease is a single-gene disorder or disease. In some embodiments, the disease is a mendelian disorder. In some embodiments, the disease is a neurological disease. In some embodiments, the disease is an autoimmune disease. In some embodiments, the disease is selected from Fragile X Syndrome (FXS), schizophrenia, bipolar disorder, psychotic bipolar disorder, dementia, fragile X-associated tremor/ataxia syndrome 1.3 (FXTAS), and FMR1-related primary ovarian insufficiency (POI), Angelman syndrome, Prader-Willi Syndrome, Beckwith-Wiedemann syndrome, Silver-Russell syndrome, lupus, rheumatoid arthritis, multiple sclerosis, diabetes and alcoholism. In some embodiments, the disease is selected from Fragile X Syndrome (FXS), schizophrenia, bipolar disorder, psychotic bipolar disorder, dementia, Angelman syndrome, Prader-Willi Syndrome, Beckwith-Wiedemann syndrome, Silver-Russell syndrome, lupus, rheumatoid arthritis, multiple sclerosis, diabetes and alcoholism. In some embodiments, the disease is selected from Fragile X Syndrome (FXS), schizophrenia, bipolar disorder, psychotic bipolar disorder, dementia, Angelman syndrome, Prader-Willi Syndrome, Beckwith-Wiedemann syndrome, Silver-Russell syndrome, and alcoholism. In some embodiments, the neurological disorder is selected from Fragile X Syndrome (FXS), schizophrenia, bipolar disorder, psychotic bipolar disorder, dementia, Angelman syndrome, Prader-Willi Syndrome, Beckwith-Wiedemann syndrome, Silver-Russell syndrome, and alcoholism. In some embodiments, the disease is an epigenetic disease. In some embodiments, the disease is an imprinting disease. In some embodiments, the imprinting disease is selected from Angelman syndrome, Prader-Willi Syndrome, Beckwith-Wiedemann syndrome, and Silver-Russell syndrome. In some embodiments, an autoimmune disease is selected from lupus, rheumatoid arthritis, multiple sclerosis and diabetes. In some embodiments, the disease is a fragile X mental retardation 1 (FMR1) gene-associated disease. In some embodiments, the FMR1-associated disease is selected from FXS, FXTAS and POI. In some embodiments, the FMR1-associated disease is FXS. In some embodiments, the disease is FXS. In some embodiments, the subject suffers from FXS.

In some embodiments, the treating comprises reactivation of at least one silenced genetic locus. In some embodiments, the treating comprises reactivation of one silenced genetic locus. Although the treatment may reactivate other genetic loci, these may be considered side effects and not required for treating the disease. In some embodiments, the treating and or reactivating does not cause cell death. In some embodiments, the treating and or reactivating does not induce apoptosis. In some embodiments, the treating and or reactivating improves the health of the cell comprising the reactivating. In some embodiments, the treating and or reactivating does not kill the cell comprising the reactivating.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the terms "administering," "administration," and like terms refer to any method which, in sound medical practice, delivers a composition containing an active agent to a subject in such a manner as to provide a therapeutic effect. One aspect of the present subject matter provides for intravenous administration of a therapeutically effective amount, DZNep alone, or in combination with of 5-azadC, to a patient in need thereof. Other suitable routes of administration can include parenteral, subcutaneous, intravenous, intramuscular, or intraperitoneal. In some embodiments, the administration comprises intracranial administration. In some embodiments, the administration comprises intrathecal administration. In some embodiments, the administration comprises intravenous administration. In some embodiments, the administration comprises intramuscular administration.

In some embodiments, a therapeutically effective dose of 5-azadC is administered. In some embodiments, a therapeutically effective dose of DZNep is administered. In some embodiments, a therapeutically effective dose of 5-azadC and DZNep is administered. In some embodiments, a therapeutically effective dose of the composition of the invention is administered. The term "therapeutically effective amount" refers to an amount of a drug effective to treat a disease or disorder in a mammal. The term "a therapeutically effective amount" refers to an amount effective, at dosages and for periods of time necessary, to achieve the desired therapeutic or prophylactic result. The exact dosage form and regimen would be determined by the physician according to the patient's condition.

The dosage administered will be dependent upon the age, health, and weight of the recipient, kind of concurrent treatment, if any, frequency of treatment, and the nature of the effect desired. In some embodiments, the dosage of 5-azadC provided is reduced due to the co-administration of DZNep. In some embodiments, the reduction is at least a 5, 10, 15, 20, 25, 30, 35, 40, 45, 50, 55, 60, 65, 70, 7, 80, 85, 90 or 95% reduction in dose. Each possibility represents a separate embodiment of the invention. In some embodiments, the reduction is at least a 30% reduction in dose.

An effective dose in mice for 5-azadC was found to be between 5-15 mg/kg/day, however, when 5-azadC was co-administered with DZNep a dose of only 5 mg/kg/day was effective. Even doses as low as 1 mg/kg/day were effective when combined with DZNep. In some embodiments, the dose of 5-azadC for treating a human is about 0.4 mg/kg/day. In some embodiments, the dose of 5-azadC for treating a human is about 0.08 mg/kg/day. In some embodiments, the dose of 5-azadC for treating a human is not more than 5, 4, 3, 2, 1, 0.9, 0.8, 0.7, 0.6, 0.5, 0.4, 0.3, 0.2, or 0.1 mg/kg/day. Each possibility represents a separate embodiment of the invention. In some embodiments, the dose of 5-azadC for treating a human is not more than 0.4 mg/kg/day. In some embodiments, the dose of 5-azadC for treating a human is not more than 0.1 mg/kg/day. In some embodiments, the dose of 5-azadC for treating a human is between 0.05 and 2, 0.05 and 1.5, 0.05 and 1.2, 0.05 and 1, 0.05 and 0.8, 0.05 and 0.6, 0.05 and 0.4, 0.05 and 0.4, 0.05 and 0.2, 0.1 and 2, 0.1 and 1.5, 0.1 and 1.2, 0.1 and 1, 0.1 and 0.8, 0.1 and 0.6, 0.1 and 0.4, 0.1 and 0.4, and 0.1 and 0.2 mg/kg/day. Each possibility represents a separate embodiment of the invention. In some embodiments, the dose of 5-azadC for treating a human is between 0.1 and 0.4 mg/kg/day. In some embodiments, a pharmaceutical composition of the invention comprises this dose of 5-azadC.

In some embodiments, the dose of DZNep for treating a human is about 1.6 mg/kg/day. In some embodiments, the dose of DZNep for treating a human is not more than 5, 4, 3, 2.8. 2.6, 2.4, 2.2, 2, 1.8, 1.6, 1.4, 1.2, 1, 0.8, 0.6, 0.4, 0.2, or 0.1 mg/kg/day. Each possibility represents a separate embodiment of the invention. In some embodiments, the dose of DZNep for treating a human is not more than 1.6 mg/kg/day. In some embodiments, the dose of DZNep for treating a human is between 1 and 5, 1 and 4, 1 and 3, 1 and 2, 1 and 1.8, 1 and 1.6, 1.2 and 5, 1.2 and 4, 1.2 and 3, 1.2 and 2, 1.2 and 1.8, 1.2 and 1.6, 1.4 and 5, 1.4 and 4, 1.4 and 3, 1.4 and 2, 1.4 and 1.8, and 1.4 and 1.6 mg/kg/day. Each possibility represents a separate embodiment of the invention. In some embodiments, a pharmaceutical composition of the invention comprises this dose of DZNep.

In some embodiments, the 5-azadC and DZNep are contacted or administered simultaneously or sequentially. In some embodiments, 5-azadC is administered first. In some embodiments, DZNep is administered first. In some embodiments, the 5-azadC and DZNep are contacted or administered simultaneously. In some embodiments, the 5-azadC and DZNep are contacted or administered any one of simultaneously, 5-azadC first and DZNep first. In some embodiments, the 5-azadC and DZNep are contacted or administered any one of simultaneously or DZNep first. In some embodiments, the 5-azadC and DZNep are administered or contacted at most 1, 2, 3 or 4 days apart. Each possibility represents a separate embodiment of the invention. In some embodiments, the 5-azadC and DZNep are administered or contacted at most 3 days apart. In some embodiments, the 5-azadC and DZNep are administered or contacted less than 1, 2, 3, or 4 days apart. Each possibility represents a separate embodiment of the invention. In some embodiments, the 5-azadC and DZNep are administered or contacted less than 3 days apart.

In some embodiments, the pharmaceutical composition comprises a pharmaceutically acceptable carrier, adjuvant or excipient. In some embodiments, the pharmaceutical composition comprises a therapeutically effective amount of 5-azadC, DZNep, or both. In some embodiments, the pharmaceutical composition comprises a dose of 5-azadC, DZNep or both such as is enumerated hereinabove.

As used herein, the term "carrier," "adjuvant" or "excipient" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. 1/Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

In some embodiments, the pharmaceutical composition of the invention is for use in reactivating transcription of a silenced genetic locus in a cell. In some embodiments, the pharmaceutical composition of the invention is for use in treating a disease or condition characterized by silenced transcription of at least one genetic locus in a subject in need thereof. In some embodiments, the pharmaceutical composition of the invention is for use in reactivating transcription of a fragile X mental retardation 1 (FMR1) gene in a cell. In some embodiments, the pharmaceutical composition of the invention is for use in treating a FMR1-associated disease in a subject in need thereof.

In some embodiments, the 5-azadC comprises a label stating the 5-azadC is for use in combination with said DZNep. In some embodiments, the DZNep comprises a label stating the DZNep is for use in combination with the 5-azadC. In some embodiments, the kit comprises both the 5-azadC and DZNep comprising labels. In some embodiments, a kit of the invention comprises instructions for combined administration By another aspect, there is provided a mouse model of FXS, the mouse model comprising an immune-compromised mouse comprising human induced pluripotent stem cells (iPSCs) derived from an FXS human.

By another aspect, there is provided a method of screening a therapeutic agent for its effectiveness in reactivating FMR1 expression or treating an FMR1-associated disease, the method comprising transplanting human iPSCs derived from a human suffering from an FMR1-associated disease into an immune-compromised mouse, administering the therapeutic agent to the mouse and measuring human FMR1 expression in the mouse, thereby screening a therapeutic agent for its effectiveness in reactivating FMR1 expression or treating an FMR1-associated disease.

In some embodiments, an increase in human FMR1 expression indicates the therapeutic agent is effective. In some embodiments, an increase in human FMR1 expression, as compared to expression after administration of a control agent, indicates the therapeutic agent is effective. In some embodiments, the control agent is DMSO. In some embodiments, an increase in human FMR1 expression, as compared to expression with no administration of an agent, indicates the therapeutic agent is effective. In some embodiments, positive expression of human FMR1 indicates the therapeutic agent is effective.

In some embodiments, the immune-compromised mouse is a SCID mouse. In some embodiments, the mouse is a NOD-SCID mouse. In some embodiments, the mouse is Il2rg null. Any mouse may be used so long as its immune system does not reject the transplanted iPSCs. In some embodiments, the mouse is not immune-compromised, and the iPSCs are non-immunogenic In some embodiments, the transplanted iPSCs are located in the location of a manifestation of the disease to be treated. In some embodiments, the transplanted iPSCs are located in the mouse brain. In some embodiments, the iPSCs are transplanted to the location the disease manifests. In some embodiments, the iPSCs are transplanted into the brain. In some embodiments, the iPSCs are transplanted into muscle. In some embodiments, the iPSCs are transplanted to a selected location in the brain. In some embodiments, they are transplanted to the hippocampus.

In some embodiments, the iPSCs are differentiated before transplanting. In some embodiments, the iPSCs are differentiated iPSCs. In some embodiments, the iPSCs are differentiated to neuronal cells. Any known neuronal differentiation protocol for iPSCs, such as the one described herein, may be used. In some embodiments, the method of the invention further comprises differentiating the iPSCs before the transplanting. In some embodiments, the iPSCs are differentiated into muscle cells. Any known muscle differentiation protocol may be employed.

In some embodiments, measuring human FMR1 expression comprises measuring FMR1 mRNA expression. In some embodiments, measuring human FMR1 expression comprises measuring FMR1 protein expression. Methods of measuring mRNA and protein expression are known in art. Use of these methods to distinguish human mRNA and/or protein from rodent mRNA/protein are also known. Primers for PCR may be designed that recognize only the human transcript (such as are provided herein in Table 1). Antibodies that bind only to human and not mouse FMR1 are commercially available from companies such as Sigma, Roche and the like.

In some embodiments, systemic FMR1 expression is measured. In some embodiments, expression at the injection site is measured. In some embodiments, expression in the transplant is measured. In some embodiments, expression in the tissue comprising the transplant is measured. In some embodiments, the transplant is removed before the measuring. In some embodiments, the measuring comprises histological analysis.

As used herein, the term "about" when combined with a value refers to plus and minus 10% of the reference value. For example, a length of about 1000 nanometers (nm) refers to a length of 1000 nm+-100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

Examples

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-II Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Cell Culture

Three human iPSC clones derived from three individual FXS patients were used during the study: patient A—clone 52, patient B—clone 40 and patient C—clone 2 (Urbach, A., Bar-Nur, O., Daley, G. Q., and Benvenisty, N. (2010). Differential Modeling of Fragile X Syndrome by Human Embryonic Stem Cells and Induced Pluripotent Stem Cells. Cell Stem Cell 6, 407-411). As a control, we used a previously characterized isogenic FXS-iPSC line with a deletion of the CGG repeat tract, induced using the CRISPR/Cas9 technology, and CSES9 hESCs and their derivatives were used as a reference for FMR1 normal expression levels (WT expression). Cell culture conditions were standard for PSC culturing. Briefly, cells were cultured on mouse embryonic fibroblasts (MEFs) in KnockOut Dulbecco's modified Eagle's medium (Invitrogen) supplemented with 15% KnockOut SR (Invitrogen), 0.1 mM β-mercaptoethanol (Sigma-Aldrich), 1% nonessential amino acids stock (Biological Industries), 1 mM glutamine, 0.1 mM 3-mercaptoethanol (Sigma-Aldrich), 50 U/ml penicillin (Biological Industries), 50 µg/ml streptomycin (Biological Industries) and 4 ng/ml FGF2 (Invitrogen). The medium was supplemented with 10 µM ROCK inhibitor (Y27632) during the first 24 hours after thawing. The cells were passaged using trypsin or trypsin-EDTA (Biological Industries, Beit Haemek, Israel).

RNA Isolation and Reverse Transcription

RNA was extracted using NucleoSpin RNA Plus kit (Macherey-Nagel) and quantified using NanoDrop 2000 (Thermo Scientific). 1 µg of RNA was reverse transcribed using ImProm-II reverse transcriptase (Promega). Quantitative RT-PCR was performed using SYBR Green qPCR Supermix (Applied Biosystems) and analyzed with the 7300 real-time PCR system (Applied biosystems). Expression of FMR1 determined using specific primers which yielded a 147 bp product spanning exons 5 and 6 of the gene. GAPDH was used for normalization. Primers used are provided in Table 1.

TABLE 1

Primer List

| Gene Name | Forward Primer | Reverse Primer |
|---|---|---|
| FMR1 | GCAGCATGTGATGCAACTTACA (SEQ ID NO: 1) | CGCCTCTTTGGCACACATT (SEQ ID NO: 2) |
| GAPDH | AGCCACATCGCTCAGACACC (SEQ ID NO: 3) | GTACTCAGCGCCAGCATCG (SEQ ID NO: 4) |

FMRP Expression Screening

Screening experiments were performed in 96-well plates, coated with Poly-L-Lysine (Sigma Aldrich) and Matrigel (BD Biosciences), using a serum free mTeSR defined medium (STEMCELL Technologies) supplemented with penicillin (50 U/ml) and streptomycin (50 µg/ml). FXS-iPSCs were plated in a density of 15,000 cells per well and cultured for 24 hours before the beginning of the treatment. Cell media was changed daily. By the end of the treatment period, cells were washed with PBS and fixated using 4% paraformaldehyde solution for 10 minutes, followed by permeabilization with 0.2% Triton X-100. After blocking with a PBS solution containing 5% fetal calf serum and 2% bovine serum albumin, the cells were incubated at 4° C. over-night with anti-FMRP (YF-MA10356, Abfrontier). Following three washes with PBS, the cells were incubated with fluorescence conjugated secondary antibodies (Alexa fluor 594; Abcam), washed three times and incubated with a 0.1% Tween 20 1% FBS solution containing 4',6-Diamidino-2-Phenylindole (DAPI) for nuclei visualization.

Fluorescence Microscopy and Image Analysis

Images were acquired using an Olympus IX81 microscope mounted with and MT20/20 illumination system and a C 10600-10B Hamamatsu camera. Automated image acquirement was performed using the ScanR acquisition system, and image analysis was conducted using the ScanR analysis system. The parameters of the imaging assay were suited in order to filter out unwanted artifacts, assessing the intensity of FMRP specific staining in a ring region surrounding the nuclear area, thus considering its proper localization.

Compounds Library

The epigenetic screening library (11076) was obtained from Cayman Chemical. The compounds were dissolved in 100% DMSO as 10 mM stock solutions.

Western Blot Analysis

Cell protein lysates were prepared using sample buffer composed of 100 mM Tris pH 6.8, 200 mM DTT, 4% SDS, 0.2% bromophenol blue and 20% glycerol. 10% polyacrylamide gel was used for protein separation. Gel was transferred to a nitrocellulose membrane. Following blocking with 5% nonfat dry milk in PBS for 1 hour, the membranes were incubated with mouse anti-FMRP antibody (YF-MA10356, Abfrontier) and rabbit anti GAPDH antibodies (2118, Cell Signaling). Following three washes the membranes were incubated with horseradish peroxidase-conjugated anti-rabbit and anti-mouse secondary antibodies (Jackson ImmunoResearch Laboratories).

Neural Differentiation

FXS-iPSCs were differentiated using a previously reported neural differentiation protocol with slight modifications. Briefly, iPSC colonies were cultured as embryoid bodies for 4 days on low attachment plates in human embryonic stem-cell media without FGF2, supplemented with 5 µM dorsomorphin (Tocris Bioscience) and 5 µM SB431542 (Cayman Chemicals). EBs were then plated for neural expansion on 0.2% gelatin-coated plates and cultured for 6 additional days in DMEM-F12 medium (Sigma) supplemented with 1×N2 (Invitrogen), 2 mM L-glutamine and 20 ng/ml FGF2 (Invitrogen). Cells were then treated with varying concentrations of 5-azadC for 6 days. Cell media was replaced daily, supplemented with fresh 5-azadC. Neuronal differentiation was performed using dual SMAD inhibition without the induction of embryoid bodies.

RNA Sequencing Analysis

Raw sequencing reads were aligned to the human genome (GRCh38/hg38) using Tophat2 and normalized FPKM values for each sample were obtained using Cufflinks. Expression threshold was defined as 0.3, elevating genes with a lower expression to this level. To select genes that were upregulated following 5-azadC treatment, we required that both repeats would have fold change of 4 over the average control expression. Functional enrichment analysis for upregulated or downregulated genes was performed using the Broad Institute's Gene Set Enrichment Analysis (GSEA) tool (software.broadinstitute.org/gsea/) (Mootha et al., 2003; Subramanian et al., 2005).

Animals

C57BL/6 female mice (Harlan) and NOD-SCID Il2rg$^{-/-}$ immunodeficient mice (Jackson Laboratory) were grown under specific pathogen-free conditions. All experimental procedures were approved by the institutional ethics committee of the Hebrew University.

FXS-Differentiated Transplants Assay

Undifferentiated FXS-iPSCs were trypsinized into single cells. ~1.5-1.6×10$^6$ cells were re-suspended in a mixture of 100p of Matrigel (Corning) and 100 µl embryonic stem cell medium and injected subcutaneously into NOD-SCID Il2rg−/− immunodeficient mice. 6 weeks after transplant initiation, mice received daily intraperitoneal injections of 5'-aza-2'-deoxycytidine (Cayman Chemicals) in a dosage of 5-15 mg/kg/day for five days. 0, 3, 6, 14 and 30 days following the treatment FXS-transplants were dissected and subjected to further analysis. Histological slides were prepared from transplant slices cryopreserved in O.C.T (Sakura Finetek) using Leica CM1850 cryostat (Leica Biosystems, 10-µM sections). The slides were fixed with cold 4% paraformaldehyde and permeabilized in blocking buffer (5% BSA, 5% normal goat serum+0.2% Triton X-100) for 1 hour at room temperature. Blocking buffer was then drained and replaced with blocking buffer supplemented with mouse anti FMRP antibody (Abfrontier, 1:500), for an overnight incubation at 4° C., followed by incubation with horseradish peroxidase-conjugated goat anti-rabbit IgG (Jackson ImmunoResearch Laboratories). Colour development was performed with DAB (3,3'-diaminobenzidine), and hematoxylin-eosin was used for histological staining of the tissue. Microscopy images were taken using an IX81 microscope (Olympus).

FXS Transplant-Derived Cell Culture

FXS-transplants were dissociated into small cell aggregates. Following further trypsinization, dissociated cells were plated on gelatin coated 6-well plates.

DNA Methylation Analysis of the FMR1 Promoter

Pyrosequencing of 22 CpGs in the FMR1 promoter was performed by EpigenDx according to standard procedures with a unique set of primers that were developed by EpigenDx (assays ADS1451FS1 and ADS1451FS2, positions (−523) to (−384) from the start site of translation of the FMR1 gene).

Transplantation of FXS-NPCs into Mouse Brain

FXS-iPSCs and edited FXS-iPSCs were differentiated into NPCs using dual SMAD inhibition, based on previously published protocols with modifications: Briefly, iPSC lines were seeded on Matrigel-coated plates (1×10$^6$ cells/well) in mTeSR medium with 10 µM ROCK inhibitor (Y27632). Differentiation was initiated by supplementing human embryonic stem cell media lacking FGF2 with 10 µM SB431542 (biogems) and 2.5 µM LDN-193189 (biogems) for 4 days. In the subsequent 5 days, medium was gradually replaced with N2 medium (DMEM/F12 supplemented with 1×N2 supplement, 50 U/ml penicillin (Biological Industries), 50 µg/ml streptomycin (Biological Industries), 1 mM glutamine, 0.2 mM ascorbic acid and 0.16% glucose) supplemented with 10 µM SB431542 and 2.5 µM LDN-193189. On day 10, cells were dissociated using TrypLE Select (Thermo Fisher Scientific) and injected into the hippocampus and the lateral ventricles of C57BL/6 female mice using a stereotaxic instrument, following anesthesia with a combination of ketamine (80 mg/kg i.p.) and xylasine (20 mg/kg i.p.) prepared in normal saline, as described previously (Fainstein et al., 2013). Three days following transplantation, animals received daily i.p. injections of 5-aza-dC (15 mg/kg/day) for 5 days. 4 days following the treatment, mice were sacrificed for histopathological analysis and RNA extraction. For histopathological analysis, mice were anesthetized using a lethal dose of phenobarbital and brains were perfused with ice-cold PBS followed by 4% paraformaldehyde. Tissues were frozen in liquid nitrogen and serial 10p coronal brain sections were cut. Adjacent sections were stained using antibodies against FMRP (mouse anti FMRP, Abfrontier YF-MA10356, 1:500) and human mitochondria (anti-mitochondria, MAB 1273, Millipore, 1:200). 4',6-Diamidino-2-Phenylindole (DAPI) was used for nuclei visualization. Secondary antibodies were used in the same concentrations as in the FMRP expression screen. For RNA extraction, mice received lethal dose of phenobarbital, and the target structures (hippocampus, lateral ventricles) were manually dissected. The tissue was mechanically disrupted, and RNA was extracted as using NucleoSpin RNA Plus kit (Macherey-Nagel).

DNMT1 Disruption Assay

As human pluripotent stem cells require DNA methylation for their viability, we used a mass transduction of FXS-iPSCs with a lentiCRISPR v2 lentiviral vector containing sgRNA that targets the open reading frame of DNMT1. The sgRNA sequence used for cloning into lentiCRISPR v2 lentiviral vector was as follows: 5'-GAGGCCAGAAGGAGGAACCG (SEQ ID NO: 5)-3'. Viruses containing these constructs were packaged and transduced. After 48 hours of selection with puromycin, cells were harvested for RNA extraction. In order to confirm DNMT1 mutagenesis in the transduced cells, we used qRT-PCR primers that were designed to have their 3' ends around the Cas9 cut-site of DNMT1, to analyze the abundance of wild-type copies to DNMT transcripts.

```
The primers were as follows:
Forward
                                   (SEQ ID NO: 6)
5'-GATCCCAGTCCCGAGTATGC-3'.

Reverse
                                   (SEQ ID NO: 7)
5'-GAGGCCAGAAGGAGGAACCG-3'.
```

Statistics

All analyses were performed using the python-based library pandas (pandas.pydata.org/). For the statistical analysis, SciPy (www.scipy.org/) and Statmodels (statsmodels.sourceforge.net/) libraries were used. Data is judged to be statistically significant when p<0.05 by two-tailed Student's T-Test.

Example 1: Nucleoside- and Non-Nucleoside DNMT Inhibitors Treatment in FXS-iPSCs Since aberrant DNA hypermethylation plays a major role in silencing FMR1 transcription, we sought to analyze the reactivating effect of a series of hypomethylating agents, inhibiting the activity of DNMTs. DNMT inhibitors are divided into nucleoside-like inhibitors and non-nucleoside inhibitors of various origins and structures. We have analyzed the effects of 4 nucleoside DNMT inhibitors (5-azacytidine, 5-aza-2-deoxycytidine, SGI-110 and Zebularine) and 5 non-nucleoside DNMT inhibitors (SGI-1027, Procainamide, Hydralazine, RG108, Disulfiram) on FMR1 expression (FIG. 1A) in FXS-iPSCs. While first and second-generation nucleoside-like inhibitors (5-azacytidine, 5-aza-2-deoxycytidine, SGI-110), with the exception of the nucleoside analogue Zebularine, were able to robustly induce FMR1 mRNA expression (FIG. 1A), non-nucleoside DNMT inhibitors were substantially less effective in their ability to reactivate the dormant gene.

Example 2: Assay Development for FMR1 Reactivation Screen

Figure 1B:
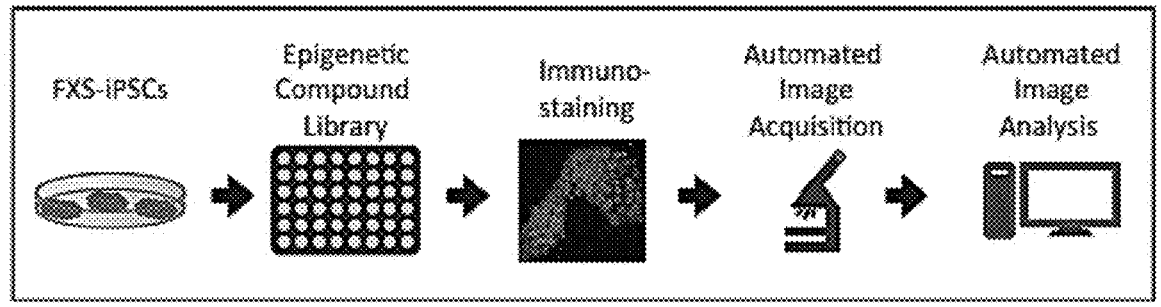
Figure 1C:
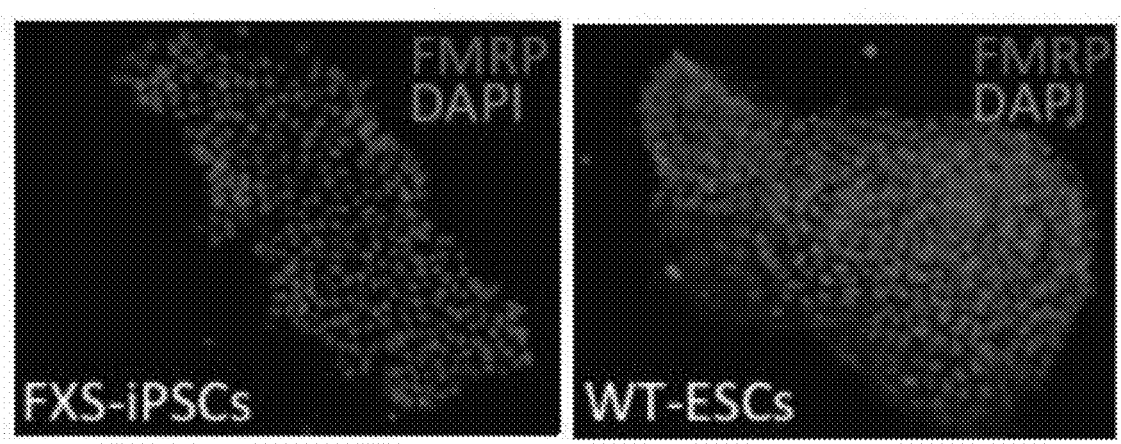
Figure 1D:
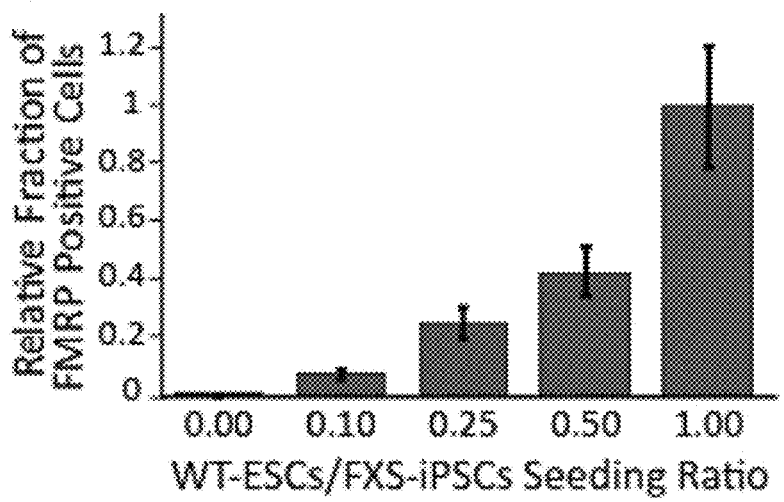
Figure 1E:
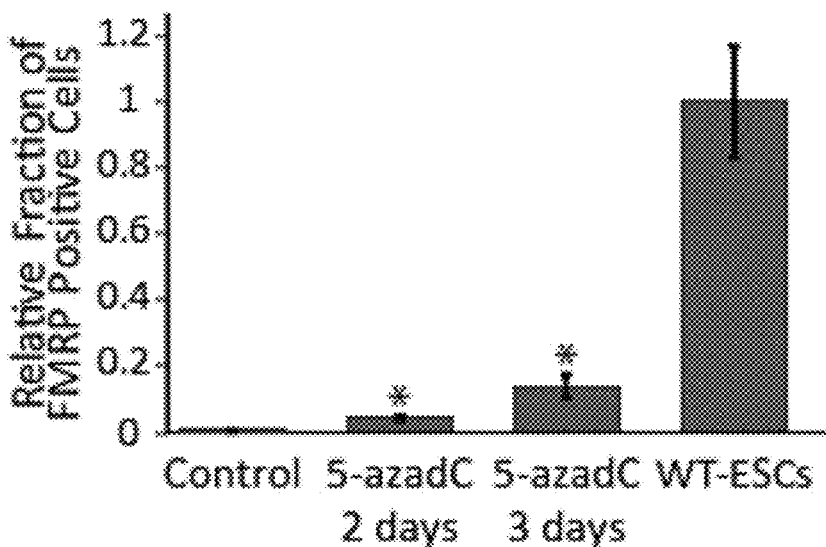

In order to analyze the ability of a larger array of epigenetic modulators to restore FMRP expression in FXS-iPSCs, we established an immunostaining-based imaging assay for the detection of FMRP in a 96-well format (FIG. 1B). For this aim, we optimized a protocol that allows the culturing and immunostaining of iPSCs in a 96-well format, followed by automated image acquisition and analysis (Table 2 For the immunostaining assay, we evaluated three different anti-FMRP antibodies. Monoclonal mouse anti FMRP antibody (Abfrontier) gave the most specific results regarding the discrimination between FXS-iPSCs and WT-ESCs (FIG. 1C-D), as well as the detection of FMRP reactivation using the demethylating agent 5'-aza-2'-deoxycytidine (5-azadC) (FIG. 1E). As the extent of FMR1 reactivation is correlated with the proportion of cells expressing FMRP, we seeded different mixtures of WT and FXS cells and validated the ability of our imaging assay to detect sub-populations of FMRP expressing cells (FIG. 1D). Automated image acquirement and analysis could also detect a time dependent increase in FMRP expression following treatment with 1 µM of the demethylating agent 5'-aza-2'-deoxycytidine (5-azadC) (FIG. 1E). 5-azadC is a derivative of 5-azacytidine which is known to have fewer side effects.

TABLE 2

Assay development for FMRP reactivation screen in a 96-well plate format.

| Parameter | Description |
| --- | --- |
| Plate | P96-1.5N-H IVS (Glass bottom dish) |
| Coating | Poly-L-Lysine and matrigel |
| Cell line | FXS-iPSCs |
| Seeding Density | 15,000 cells per well |
| Compound Concentration | 2 uM, 20 uM |
| Time Coarse | 72 h treatment |
| Primary Antibody | Abfrontier YF-MA10356 Mouse anti FMRP (1:200, 4° C. overnight) |

TABLE 2-continued

Assay development for FMRP reactivation screen in a 96-well plate format.

| Parameter | Description |
| --- | --- |
| Secondary Antibody | Alexa Fluor 488 Donkey anti Mouse (1:800, 25° C. 1 hour) |
| Positive Control | 5-aza-dC (2 uM) |
| Negative Control | DMSO |

Example 3: Screening of a Focused Epigenetic Library

Figure 1F:
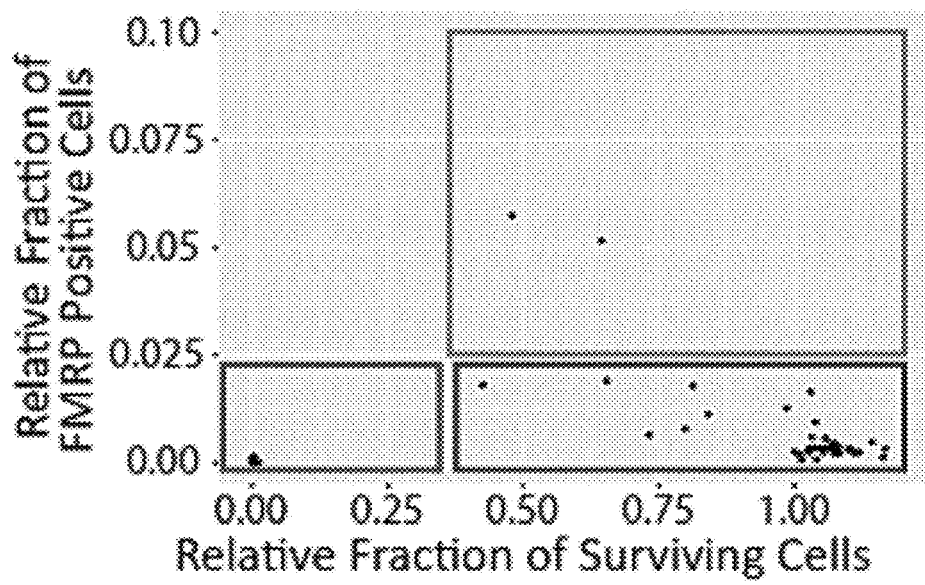
Figure 1G:
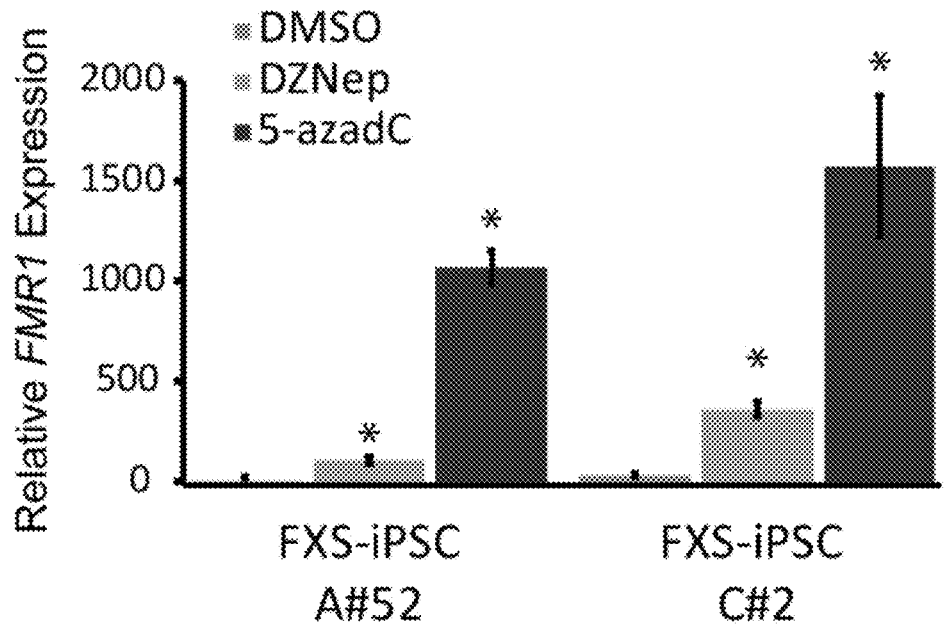
Figure 1H:
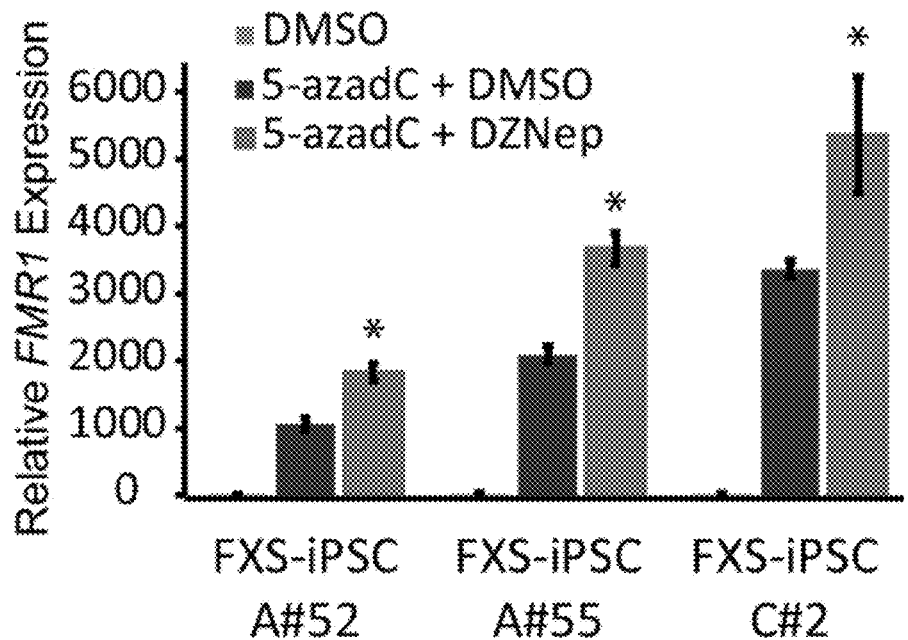
Figure 1I:
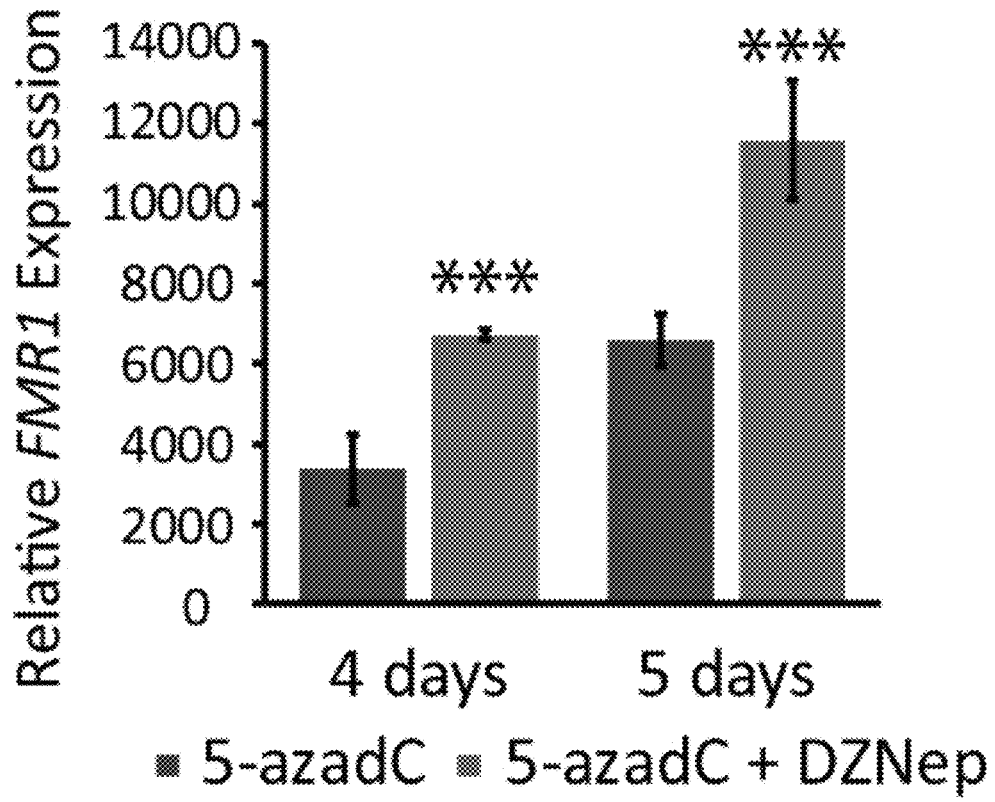
Figure 1J:
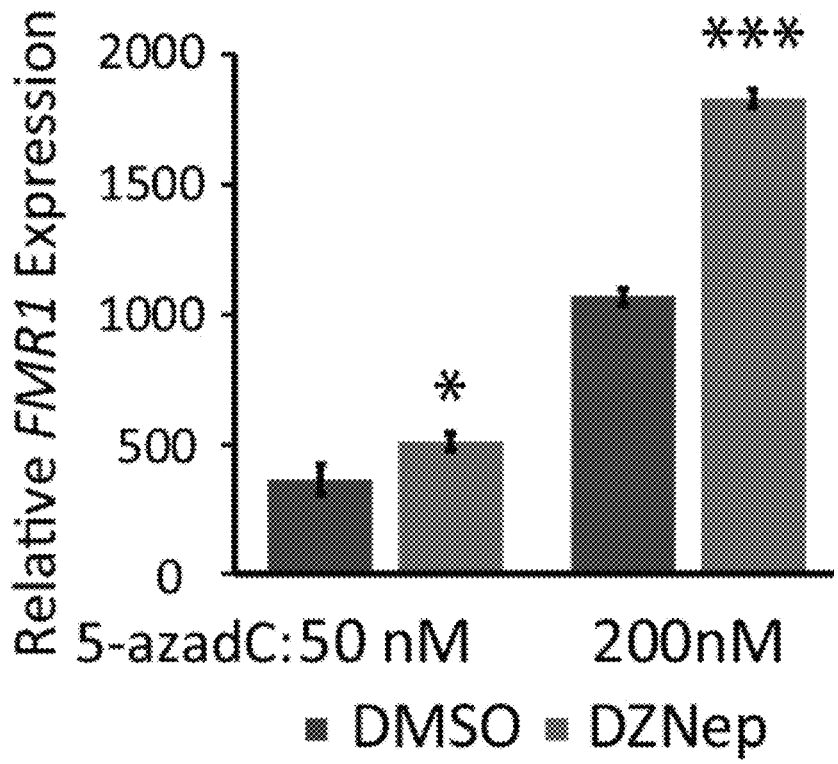
Figure 1K:
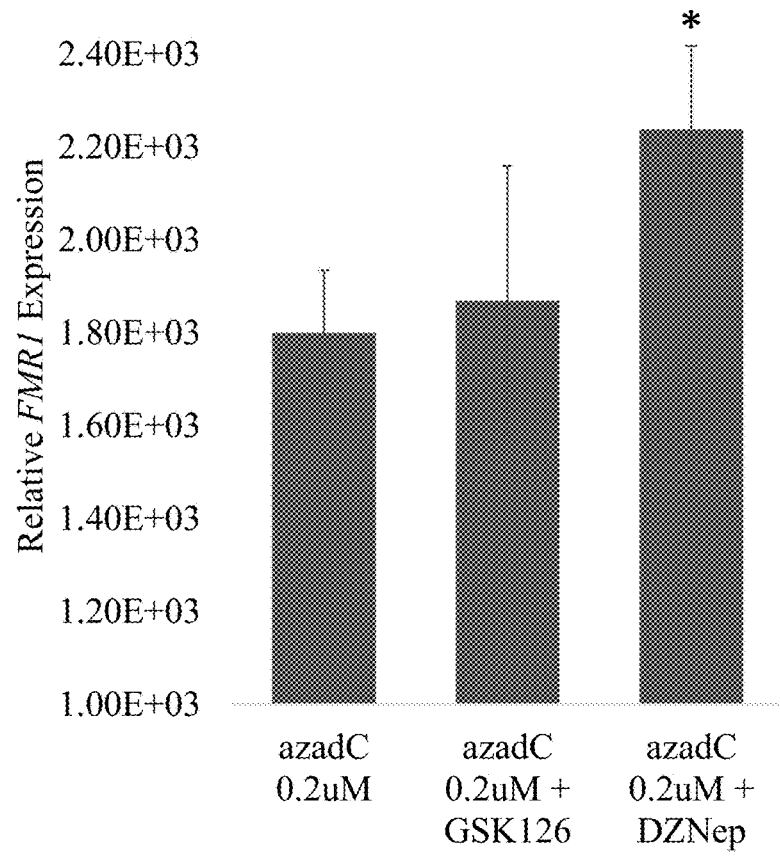

Following the development of FMRP reactivation assay, we initiated a screen of a focused epigenetic small molecules library, containing modulators of various epigenetic effectors. We tested a set of 140 compounds in two concentrations (2 µM and 20 µM), with a treatment course of 72 hours (FIG. 1F). Using our automated imaging assay, we identified 19 compounds that induced a small FMRP signal increase. As expected, 5-azadC, which is contained in the library, was identified among the positive hits. The positive hit compounds, along with 26 more compounds that were too toxic in the concentrations used in the 96-well assay, were tested in a secondary assay using quantitative RT-PCR to measure FMR1 expression. Several compounds were able to induce modest levels of FMR1 expression, the most potent of which was 3-Deazaneoplanocin A (DZNep), an S-adenosyl-homocysteine hydrolase inhibitor and a histone methyltransferase (HMT) EZH2 inhibitor (FIG. 1G). Interestingly, the 140-compound panel included a number of HMT inhibitors and several, such as UNC1999, had no positive effect on FMRP reactivation. Nevertheless, the identified agents were less effective than nucleoside DNMT inhibitors, which remained the most efficient agents for reversing FMR1 inactivation. As no hit compound was potent enough to replace 5-azadC as a single treatment, we hypothesized that combining a nucleoside DNMT inhibitor with a compound that acts through a different mechanism may potentiate the effect of the demethylating treatment and decrease the levels of 5-azadC required for a robust induction of FMR1 expression. Indeed, treatment with 3-Deazaneoplanocin A in combination with 5-azadC, significantly potentiated the effect of 5-azadC on FMR1 expression in three different FXS-iPSC lines (FIG. 1H-J). The variability in FMR1 reactivation levels among different FXS-iPSC lines can be attributed to differences in CGG repeats number, DNA methylation and chromatin modifications landscape of the expanded locus, as well as to other cell line specific features, such as proliferation rate. Combination of DZNep with a different HMT inhibitor, GSK126, produced inferior FMR1 expression (FIG. 1K).

Figure 1L:
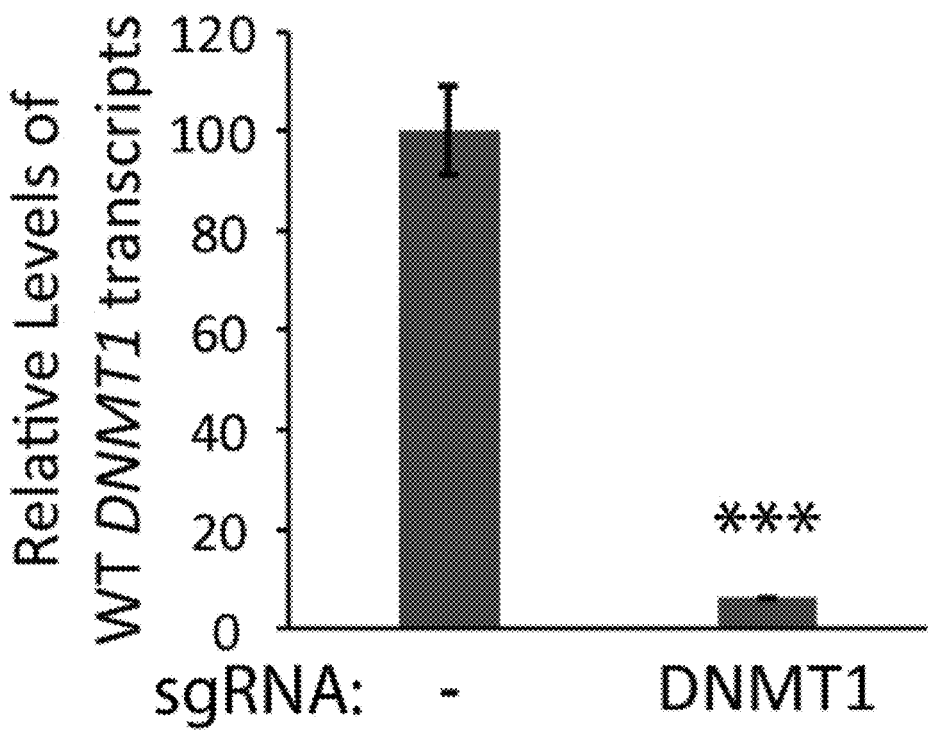
Figure 1M:
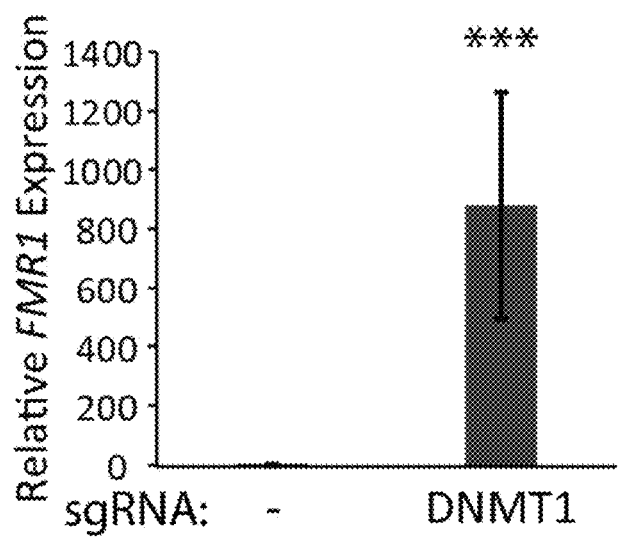

Example 4: Molecular Analysis of Direct Demethylation Effects in FXS-Affected Neural Cells As DNA demethylation remained the most potent mechanism for activating the silenced FMR1 locus, we sought to better characterize the rescue effect observed following this treatment. To validate the ability of direct disruption of DNMTs to reactivate FMR1 expression, we used CRISPR-Cas9 mutagenesis of DNMT1 in FXS-iPSCs. RT-PCR analysis of FXS-iPSCs following transduction with a lentiviral vector targeting DNMT1 has shown a reduction in the wild-type transcript levels of DNMT1, as well as restoration of FMR1 expression (FIG. 1L-M).

Figure 2A:
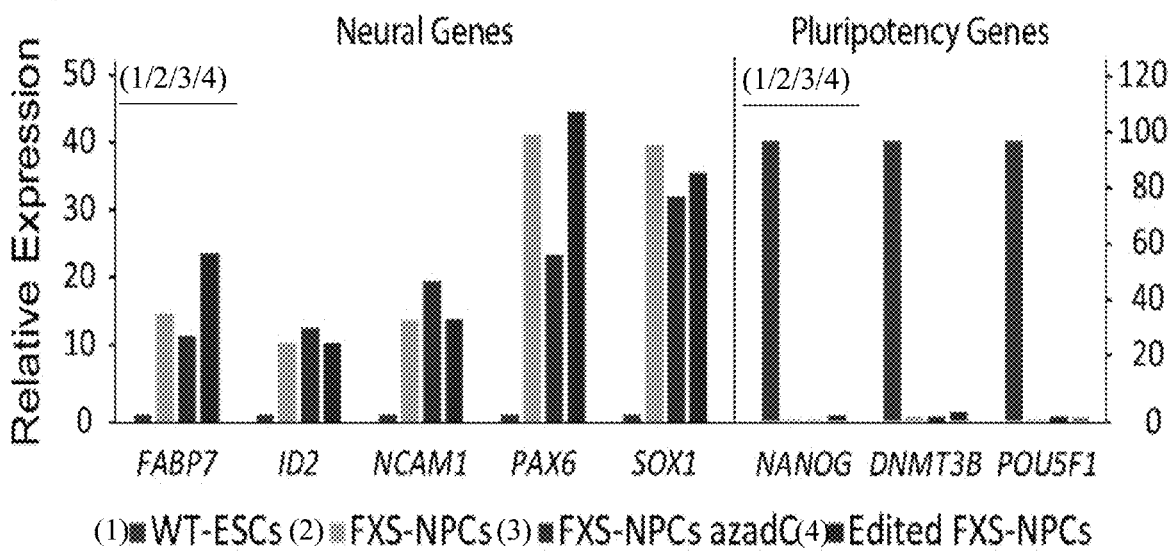
FIGS. 2A-P: Molecular analysis of direct FMR1 demethylation in vitro. (2A) A bar graph of RT-PCR analysis of neural and pluripotency marker gene expression in WT-ESCs, corrected FXS-NPCs, 5-azadC treated and untreated FXS-NPCs. (2B) A line graph showing the long-term effects of FMR1 reactivating treatment in FXS-NPCs. FXS-NPCs were treated with either DMSO (control) or 5 μM 5-azadC for 6 days. RT-PCR analysis of FMR1 mRNA levels was performed 1,6,14 and 30 days after treatment withdrawal. (2C) A bar chart depicting gene expression analysis of neural genes that are aberrantly downregulated in FXS-NPCs, and are restored following 5-azadC treatment, as detected by RNA sequencing of two biological replicates per sample. (2D) A line graph of RT-PCR analysis of FMR1 mRNA levels in FXS-NPCs after 96-hour treatment with different 5-azadC concentrations. Values represent the percent of FMR1 expression in WT cells. (2E) A bar graph showing DZNep potentiates the effect of demethylating treatment compared with 5-azadC alone in FXS-NPCs. Cells were treated with 5-azadC (100 nM) alone, or with a combination of 5-azadC and DZNep (25 uM). (2F) The left panel shows western blot analysis of FMRP expression in FXS-NPCs, 5-azadC treated FXS-NPCs 14 and 35 days post 5-azadC withdrawal, and WT-NPCs. The right panel is a bar chart of the quantification of FMRP expression (from the left panel) normalized to GAPDH, using ImageJ. (2G) Western blot analysis of FMRP expression in FXS-NPCs, 5-azadC treated FXS-NPCs 14 and 35 days post 5-azadC withdrawal, and WT-NPCs, as detected by a different anti-FMRP antibody (Abcam). (2H) A bar chart of the changes in FMR1 expression levels in FXS-NPCs after 5-azadC treatment, as detected by RNA sequencing. (2I) Micrographs of immunofluorescent staining of FXS-neurons and FXS-iPSCs for the proliferation marker Ki67 (top panels), and immunofluorescent staining of FXS-neurons for the neuronal marker TUJ1 (bottom panel). (2J) A bar chart showing changes in FMR1 expression levels in FXS-neurons after 48 hours of 5-azadC treatment, as detected by RT-PCR. (2K) Scatter plot of expression differences between 5-azadC treated FXS- NPCs and untreated FXS-NPCs (two biological replicates per condition). The FMR1 gene (black arrow) was among the 50 most upregulated genes following the treatment. (2L) Heatmap of X chromosome genes that were significantly upregulated following 5-azadC treatment of FXS-NPCs, in edited FXS-NPCs, 5-azadC treated FXS-NPCs, untreated FXS-NPCs, untreated pES6 ESCs and 5-azadC treated pES6 ESCs. (2M) A bar graph of enrichment categories of significantly upregulated genes following 5-azadC treatment, as analysed by the GSEA software. (2N) A bar graph of positional gene set enrichment categories for genes upregulated following 5-azadC treatment in FXS-NPCs analysed using the GSEA software. (2O) A bar graph of the percentage of upregulated genes per chromosome following 5-azadC treatment of FXS-NPCs. (2P) The response to demethylating treatment according to the X chromosome inactivation (XCI) status. X chromosome genes with a known XCI status that were unexpressed in our samples (average FPKM in FXS-control samples <0.5 FPKM). Upregulated genes are those in which both 5-azadC treatment repeats were 4-fold higher than the average expression in FXS-control samples. *$p<0.05$, ***$p<0.001$. Statistical tests were performed with three independent experiments. Error bars represent SEM.
Figure 2B:
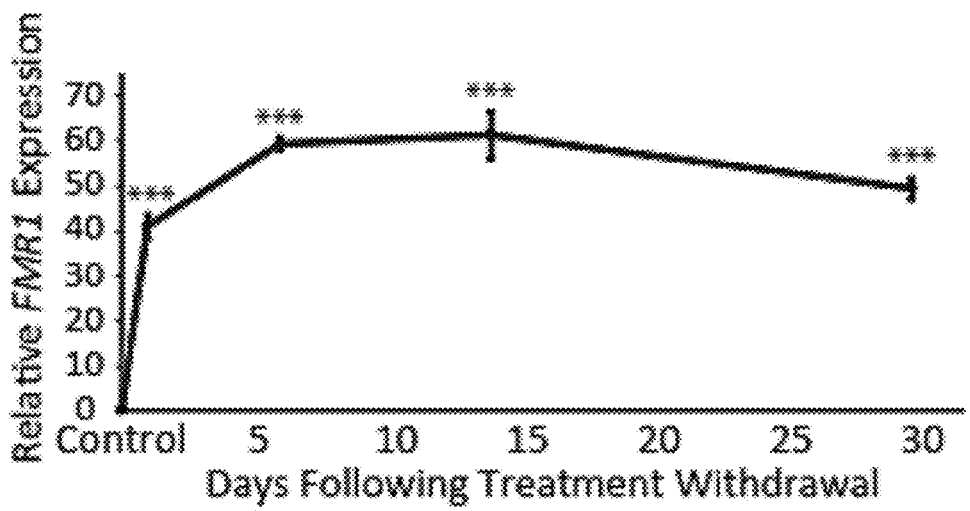
Figure 2C:
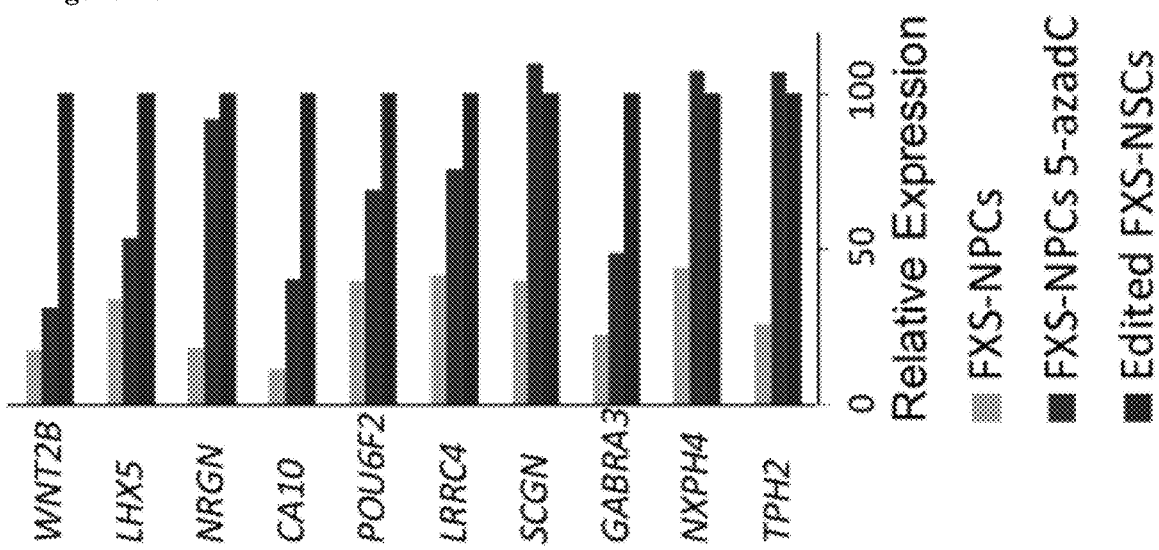
Figure 2D:
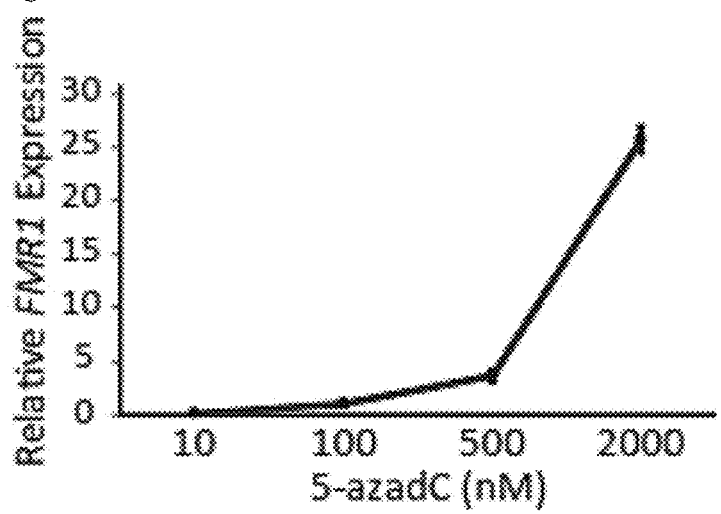
Figure 2E:
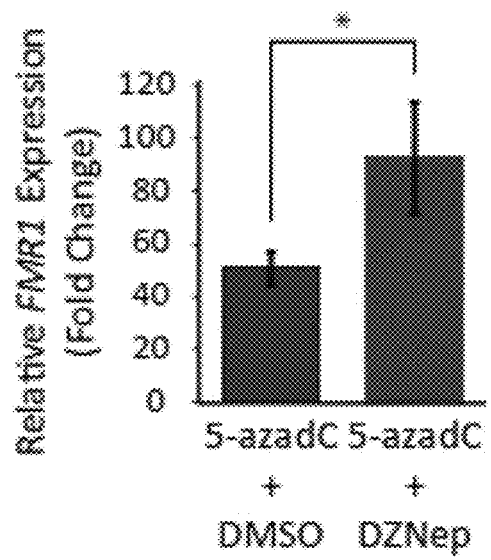

Next, to analyze the treatment effects in a neural cell type, we differentiated into neural precursor cells (NPCs) both FXS-iPSCs and an isogenic edited FXS-iPSC line, which lacks the CGG repeats segment and expresses FMRP (FIG. 2A). 5-azadC was used as the nucleoside DNMT inhibitor of choice due to its specific mode of action, avoiding the possible secondary effects of RNA incorporation seen with 5-azaC. 5-azadC treatment of FXS-iPSC-derived NPCs resulted in the restoration of FMR1 mRNA levels to approximately 40% of that in the isogenic edited-FXS cell line (FIG. 2B), that was accompanied by the upregulation of a subset of neural genes perturbed in FXS-NPCs (FIG. 2C). Interestingly, while 5-azadC treatment was associated with significant toxicity in iPSCs, FXS-NPCs did not show any changes in viability following the treatment. 5-azadC treatment reactivated FMR1 expression in a dose dependent manner (FIG. 2D). Similar to FXS-iPSCs, combined treatment of 5-azadC and DZNep potentiated the extent of FMR1 reactivation in FXS-iPSC derived NPCs, as compared with 5-azadC treatment alone (FIG. 2E).

Figure 2F:
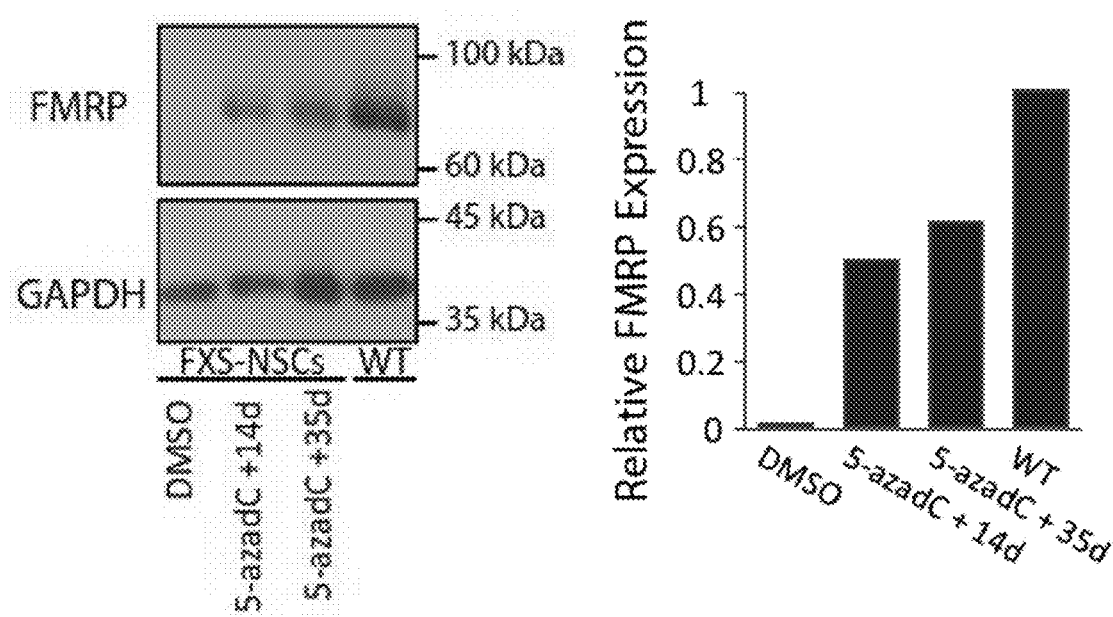
Figure 2G:
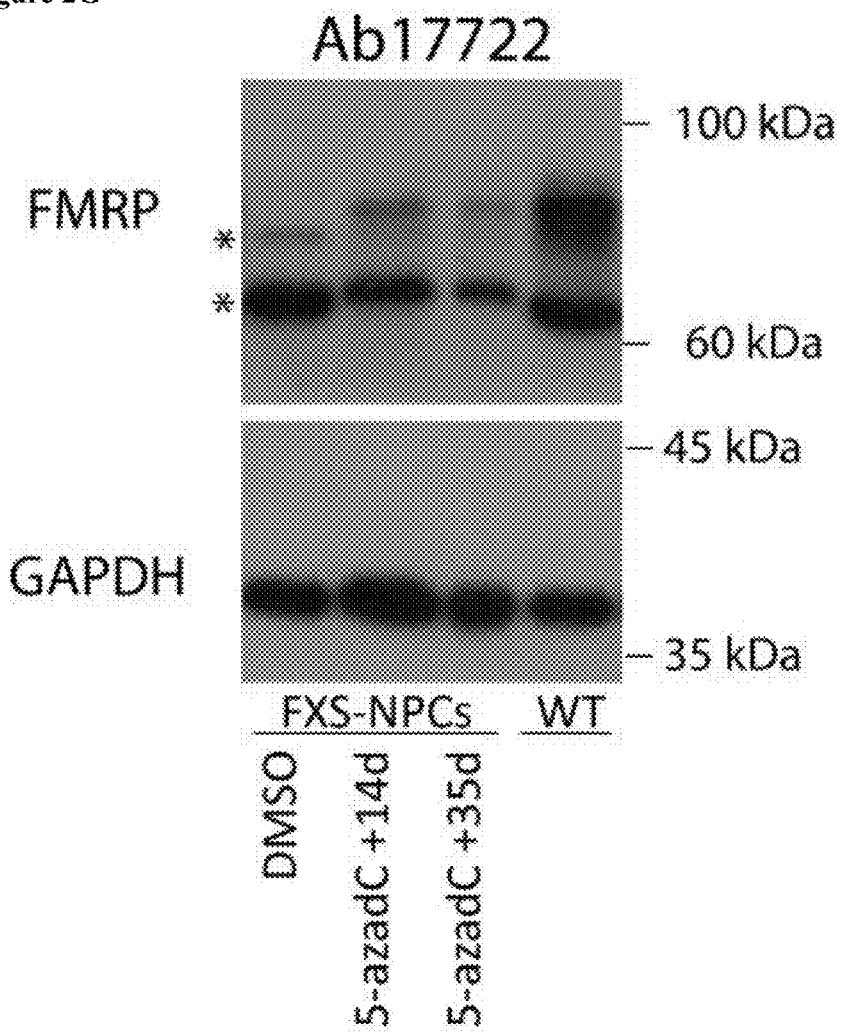
Figure 2H:
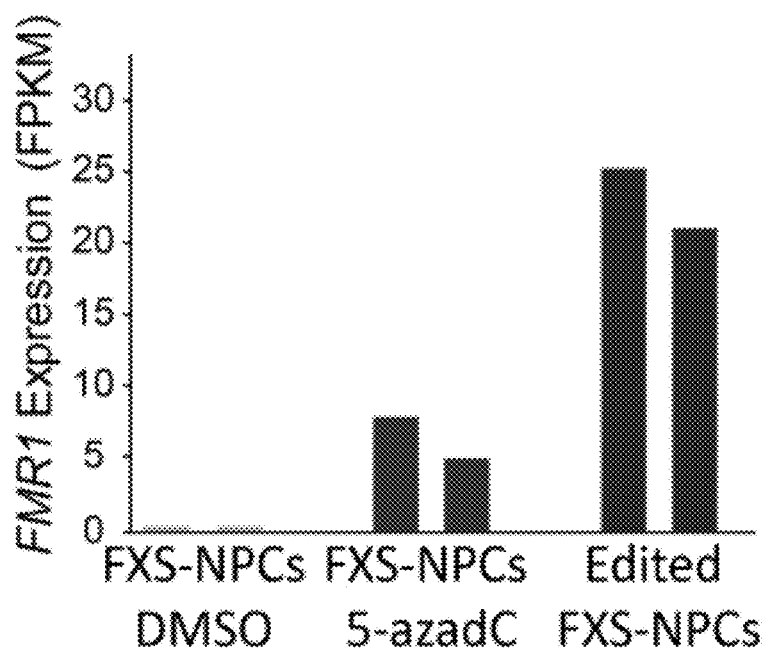
Figure 2I:
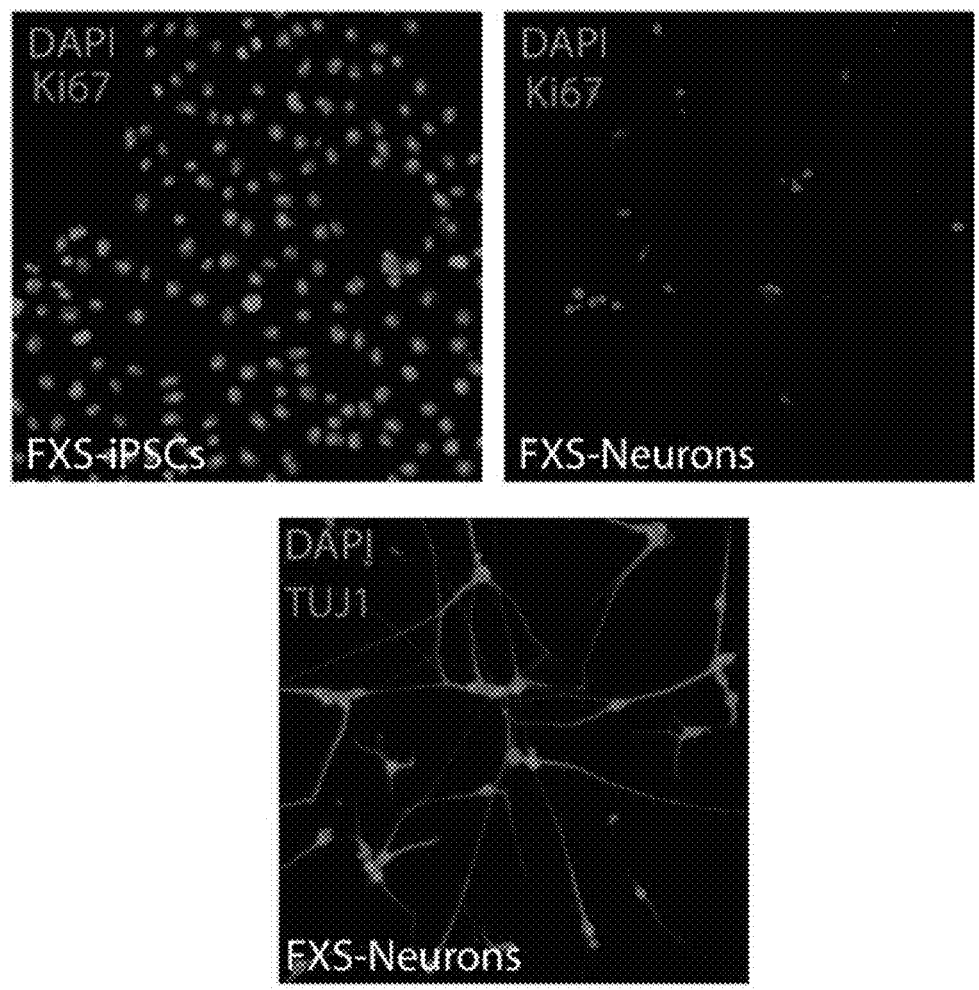
Figure 2J:
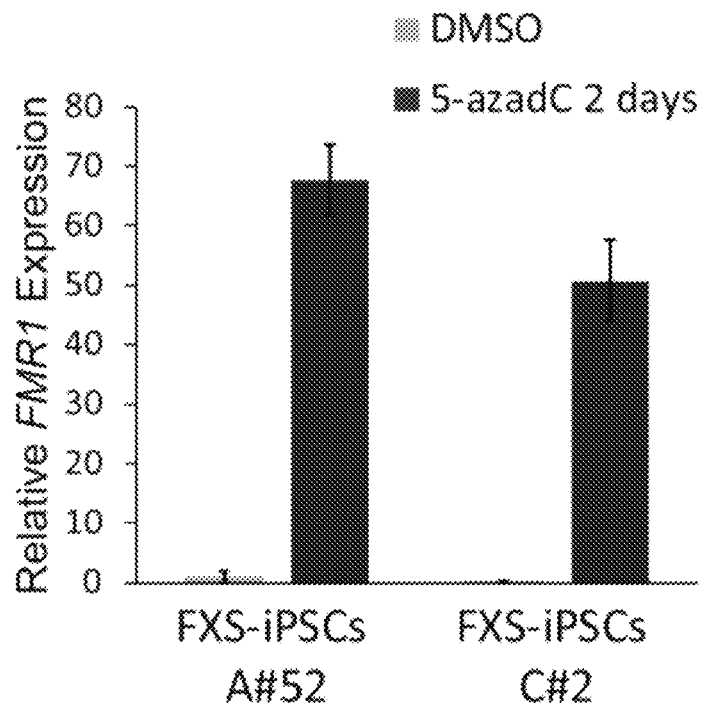

One of the most important questions regarding the feasibility of FMR1 reactivating therapy is whether FMR1 expression would be maintained following treatment withdrawal. Therefore, we sought to evaluate the temporal dynamics of the demethylation effect by measuring the levels of FMR1 expression at different time points following treatment withdrawal. In 5-azadC treated FXS-NPCs, FMR1 mRNA reached 40% of normal cells following 6 days of treatment and increased to a maximum of 60-70% of normal cells 6 days after the drug was removed (FIG. 2B). Treated FXS-NPCs did not show any decline in FMR1 expression during the entire culturing period following 5-azadC withdrawal, as was shown by real-time PCR analyses 30 days after the end of the treatment (FIG. 2B). This transcriptional activity was accompanied by FMRP expression, detectable in similar levels 14 and 35 days after treatment withdrawal (FIG. 2F-H). 5-azadC treatment was also able to induce modest levels of FMR1 expression in terminally differentiated neuronal cultures (FIG. 2I-J). Although the reactivation extent was significantly smaller than in neural progenitor cells, suggesting the feasibility of reactivating treatments also in more mature populations of neuronal cells.

Figure 2K:
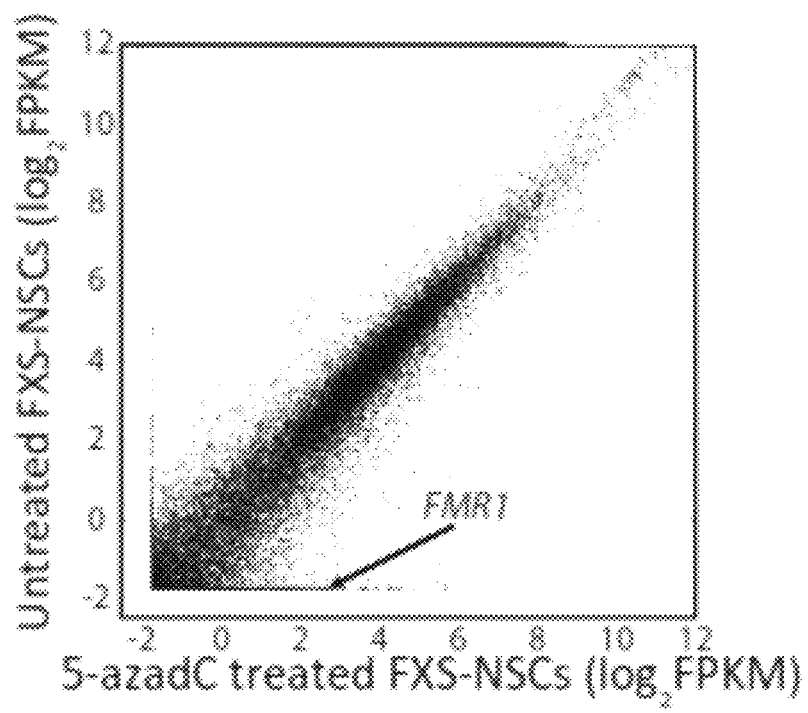
Figure 2L:
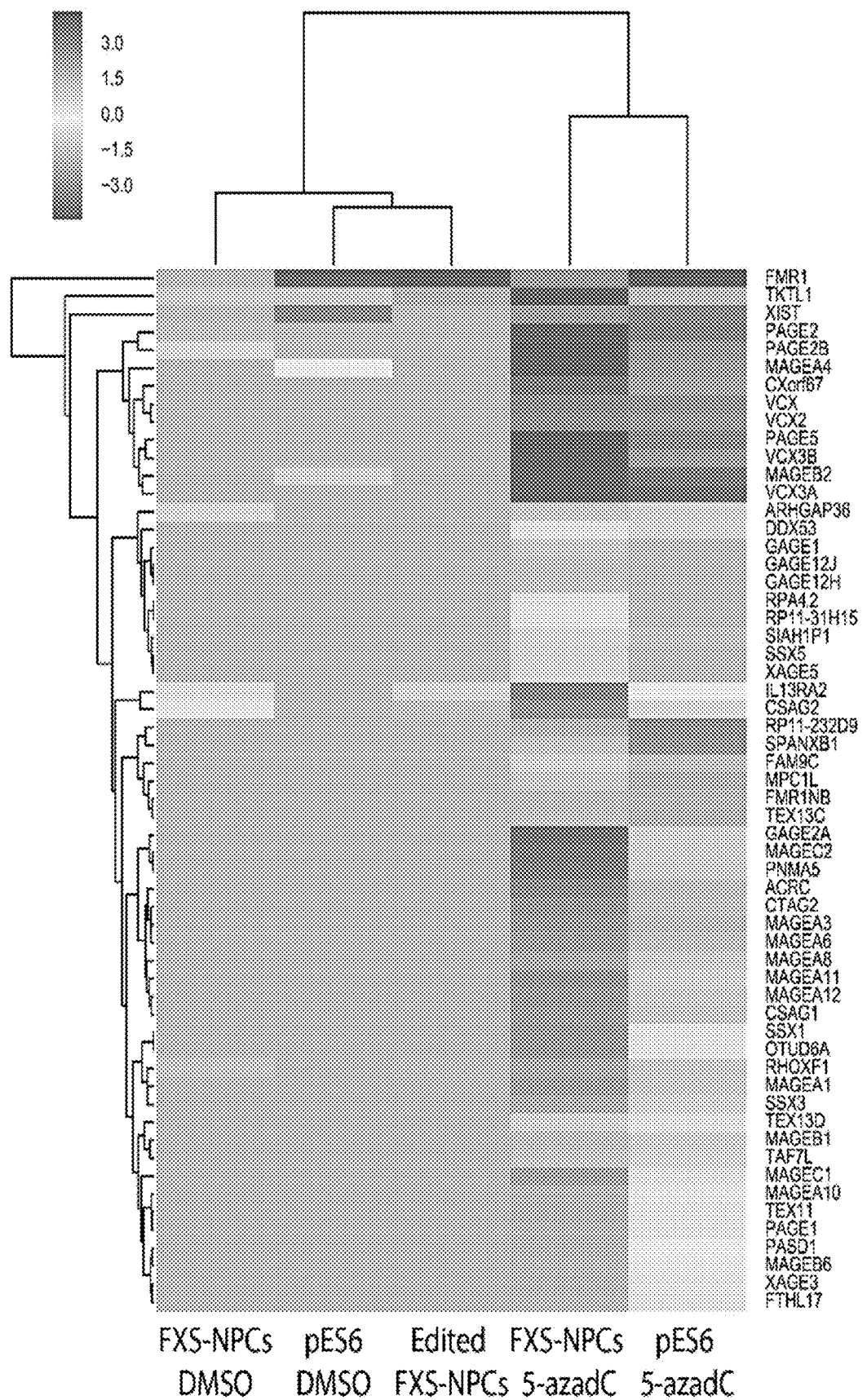
Figure 2M:
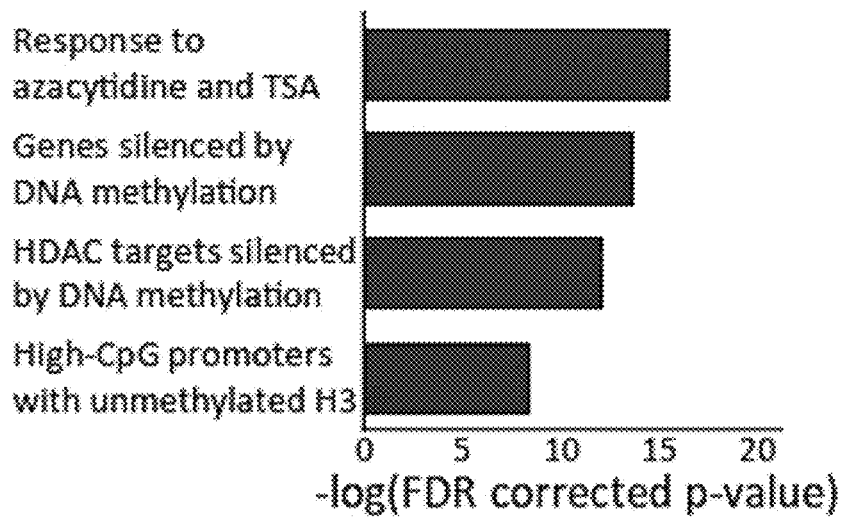
Figure 2N:
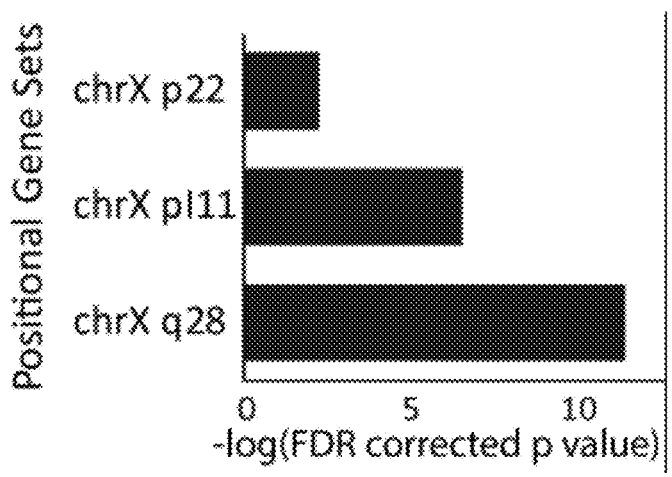
Figure 2O:
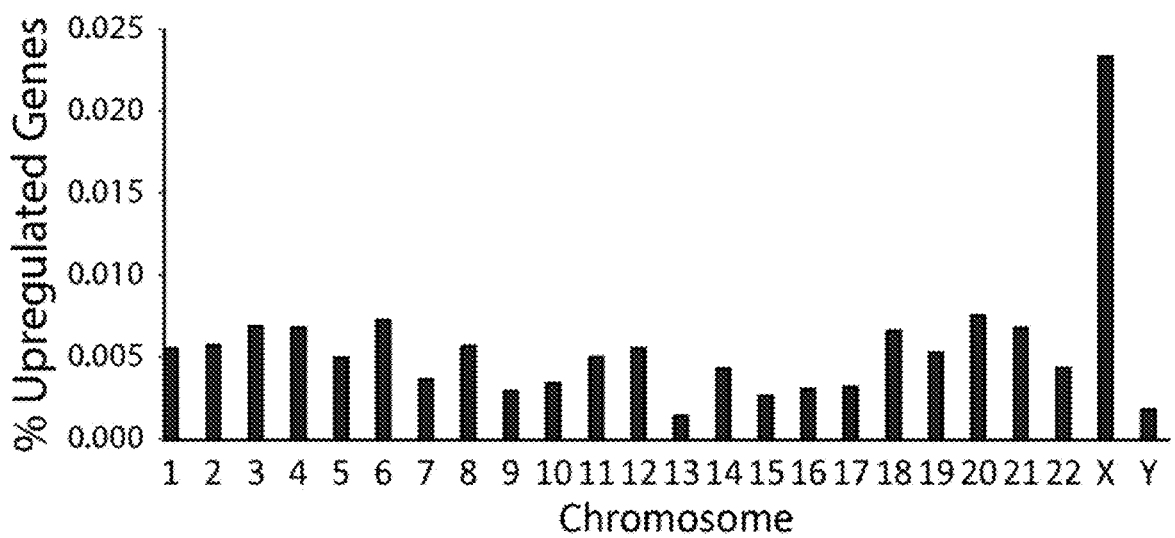
Figure 2P:
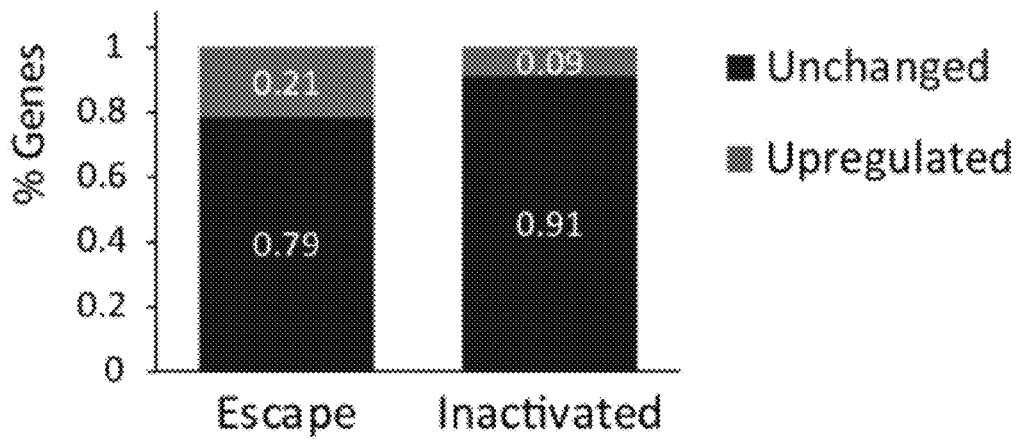

Next, we turned to analyze the global expression changes following 5-azadC treatment of FXS-NPCs. Transcriptome analysis of FXS-NPCs, 5-azadC treated FXS-NPCs, and edited FXS-NPCs showed that the expression of 348 genes substantially changed following the treatment (fold change >4 in both repeats), with FMR1 being one of the top-50 most upregulated genes (FIG. 2K-L). Gene set enrichment analysis (GSEA) revealed a significant enrichment of genes which are targets of DNA methylation and histone deacetylases, and of genes previously identified as responsive to demethylating treatment (FIG. 2M). Interestingly, positional gene set enrichment analysis revealed an enrichment of genes located in several loci on the X chromosome (chrXp22, chrXp11, and chrXq28, FIG. 2N). Overall, the relative number of upregulated genes on the X chromosome was about 4-fold higher than on any other chromosome (FIG. 2O). In order to determine whether this phenomenon was specific to the FXS phenotype, we utilized an RNA-sequencing analysis of an ESC line (pES6) treated with 5-azadC (Weissbein et al., 2017, Culture-induced recurrent epigenetic aberrations in human pluripotent stem cells. PLOS Genet. 13, e1006979). We found that most of the X chromosome genes that were significantly upregulated following the treatment in male FXS-NPCs, were also upregulated in the female pES6 cell line (FIG. 2L), suggesting that the increased sensitivity for demethylating treatment in X chromosome genes is due to an intrinsic bias in these genomic regions, rather than an FXS-specific effect. Next, we have hypothesized that the sensitivity for demethylating treatment in X chromosome genes might be correlated with inherent epigenetic features, such as their tendency to undergo X chromosome inactivation (XCI). In order to classify the upregulated genes according to their XCI status, we utilized a database that combined the analysis of three prior studies and examined XCI across 27 human tissue types using various approaches (Tukiainen et al., 2017, Landscape of X chromosome inactivation across human tissues. Nature 550, 244-248). We classified genes with a known XCI status, that were not expressed in the untreated FXS-NPCs, according to their response to demethylating treatment. Interestingly, the percentage of upregulated genes was 2.33 fold higher in genes that escape from XCI, compared to genes that undergo XCI, suggesting that the sensitivity of genes to the cellular levels of DNMTs is dependent, at least in part, on their innate epigenetic regulation (FIG. 2P).

Example 5: Establishment of an In Vivo System for Testing Reactivating Treatments Although in vitro experiments have demonstrated the ability of several compounds to reactivate FMR1 in affected cell lines, the lack of an authentic animal model for the CGG expansion mediated inactivation of FMR1 precludes the assessment of reactivating therapy in vivo.

Figure 3A:
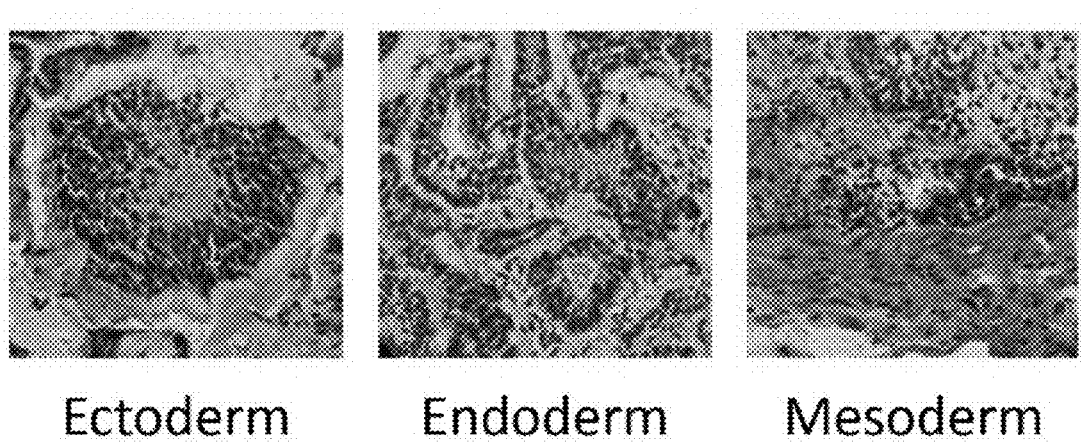
FIGS. 3A-M: Demethylating Treatment of Humanized Mice Carrying FXS-Transplants. (3A) Micrographs of sections of transplants generated from FXS-iPSCs, following 5-azadC treatment, presenting derivatives of all three germ layers: ectoderm (left panel), endoderm (middle panel) and ectoderm (right panel). (3B) Schematic representation of in vivo experiment. Undifferentiated FXS-iPSCs were injected subcutaneously into NOD-SCID Il2rg$^{-/-}$ immunodeficient mice. 6 weeks following the injection, the mice received 5 intraperitoneal injections of 5-azadC in a dosage of 5-15 mg/kg/day. FXS-transplants were extracted 0, 3, 6, 14 and 30 days following the treatment (n=3 for each time point). (3C) A heatmap representation of pyrosequencing analysis of DNA methylation of the FMR1 promoter (in 17 CpG positions) following 5 days (top group), or 30 days (middle group) of systemic 5-azadC treatment, or DZNep (20 mg/kg/day) and 5-azadC (5 mg/kg/day) (bottom group) in FXS-affected transplants, derived from two FXS-iPSC lines (A #52, C #2). AZA high=15 mg/kg/day. AZA low=5 mg/kg/day. (3D) A bar graph of RT-PCR analysis of FMR1 mRNA expression in differentiated FXS-C #2 iPSC-derived transplants in NOD-SCID Il2rg−/− mice, 1, 3, 6, 14 and 30 days following systemic treatment with 5-azadC, normalized relative to WT-transplants. (3E) A bar graphs of RT-PCR analysis of FMR1 mRNA expression in differentiated FXS-A #52 iPSC-derived transplants in NOD-SCID Il2rg−/− mice, 1, 3, 6, and 14 days following systemic treatment with 5-azadC, normalized relative to WT-transplants. (3F) A bar graph showing RT-PCR analysis of FMR1 mRNA expression in differentiated FXS-A #52 iPSC-derived transplants, treated by different concentrations of 5-azadC for 5 days (3G) Micrographs of immunohistochemical staining (3,3'-diaminobenzidine) for FMRP in untreated and 5-azadC treated FXS-transplanted. Serial sectioning of FXS-transplants revealed that FMRP expression was confined to primitive neural structures, identified by their rosette-like structure of radial and multilayered arrangement of epithelial cells. (dashed line). (3H) Micrographs of immunofluorescent staining for FMRP (red) and the neural marker NCAM1 (green) in untreated and 5-azadC treated FXS-transplants. FMRP expression was induced in primitive neural structures within FXS-transplants (3I) A bar graph of RT-PCR analysis of FMR1 expression in FXS-transplant-derived cell lines. 5-azadC treated FXS-transplants were dissociated and plated on tissue culture plates and treated with either DMSO or DZNep (25 uM) for 4 days. The values are normalized relative to FXS affected cells. (3J) A bar graph of RT-PCR analysis of FMR1 expression in FXS-transplants treated by either a combination of DZNep (20 mg/kg/day) and 5-azadC (5 mg/kg/day) or by 5-azadC alone for 5 days. The values are normalized relative to FXS affected cells. (3K) A bar graph representation of pyrosequencing analysis of DNA methylation in the FMR1 promoter (in 17 CpG positions) in FXS-transplants following treatment by either a combination of DZNep (20 mg/kg/day) and 5-azadC (5 mg/kg/day) or by 5-azadC alone for 5 days. (3L) A bar graph representation of pyrosequencing analysis of DNA methylation in the FMR1 promoter (in 17 CpG positions) following DZNep treatment in two FXS-iPSC lines (A #52, C #2). (3M) Heatmap representation of pyrosequencing analysis of DNA methylation in 17 CpG positions across the FMR1 promoter, before and after DZNep treatment in FXS-iPSCs. *$p<0.05$, *** $p<0.001$. Statistical tests were performed with three independent experiments. Error bars represent SEM.
Figure 3B:
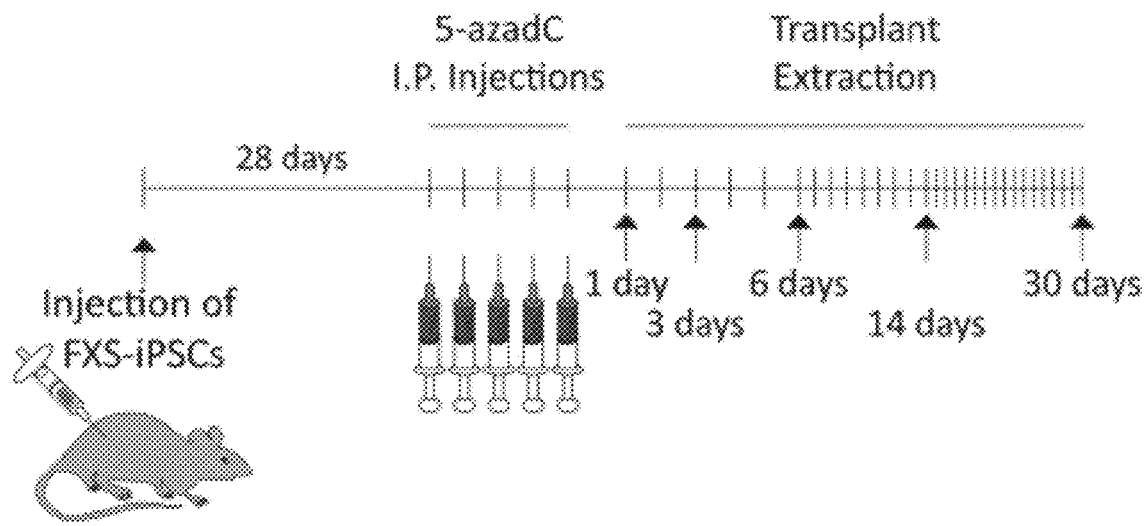
Figure 3C:
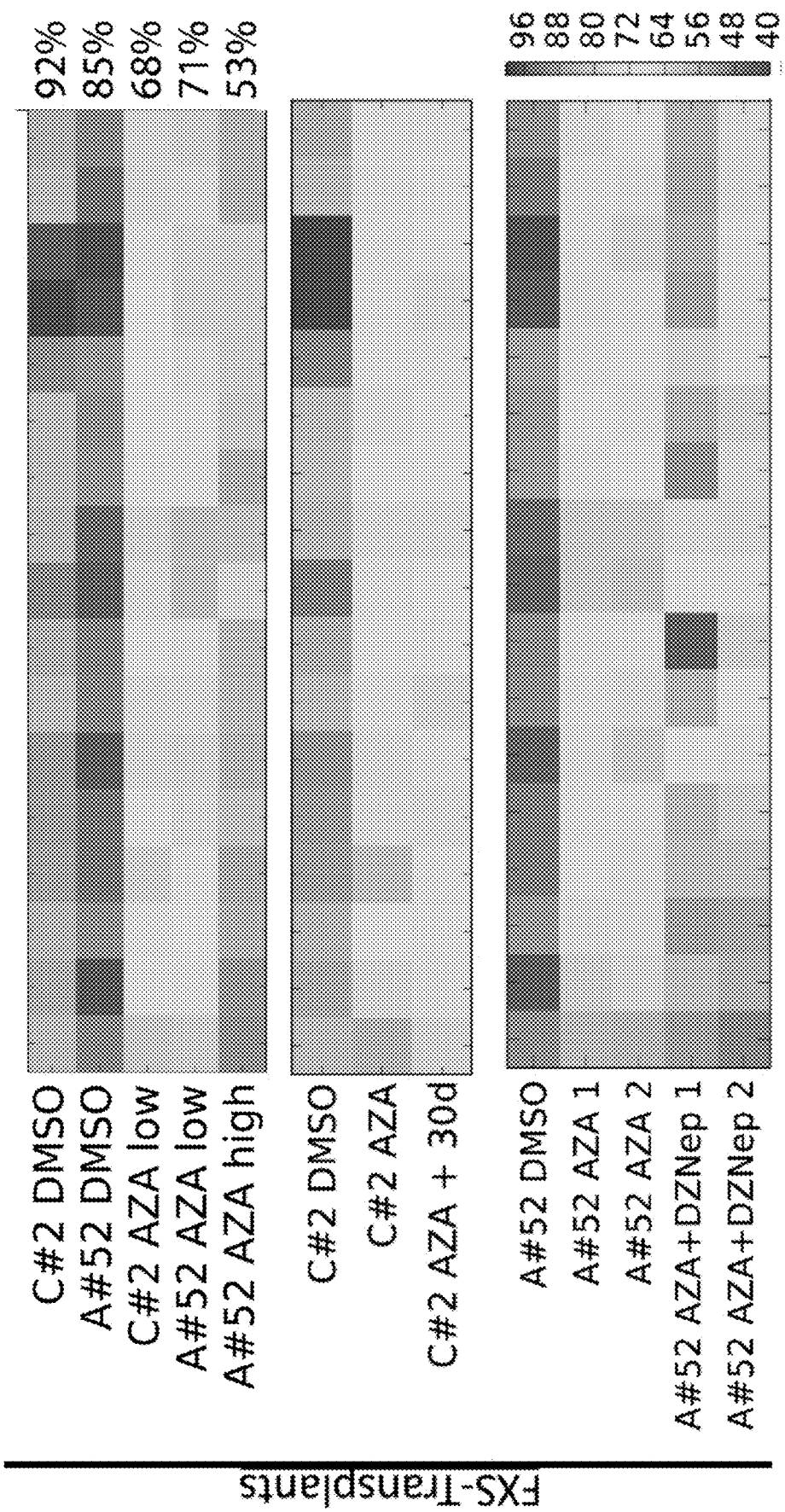
Figure 3D:
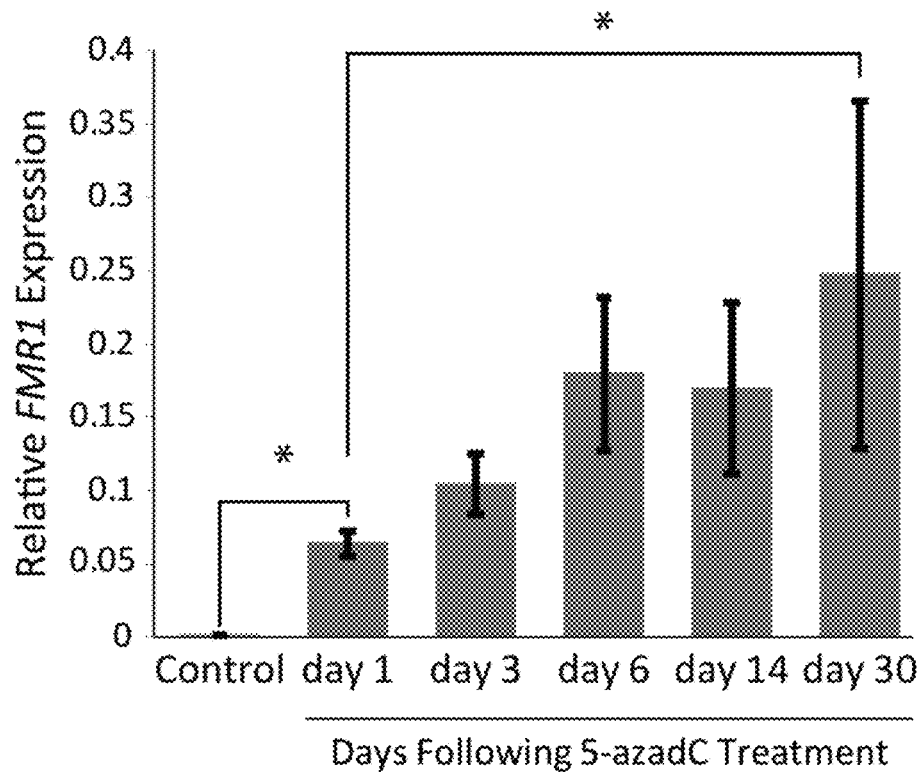
Figure 3E:
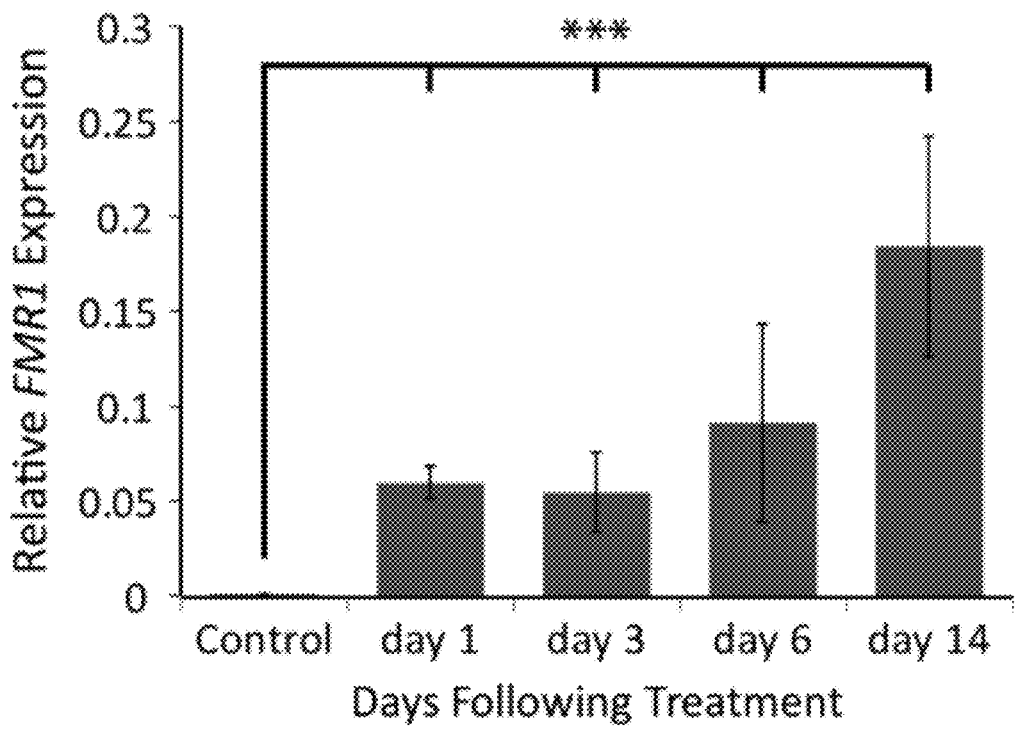
Figure 3F:
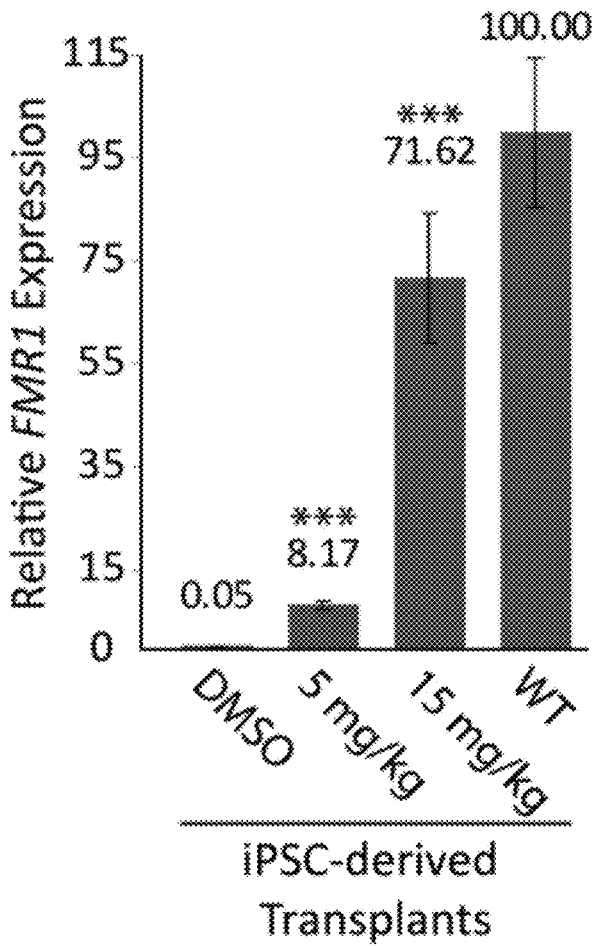
Figure 3G:
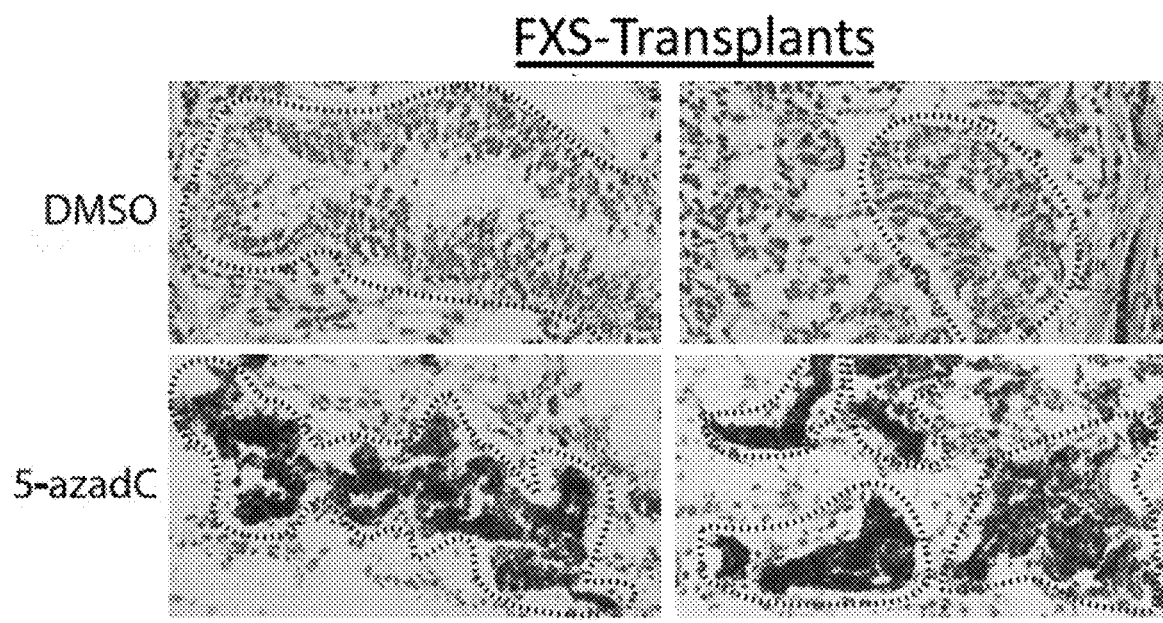
Figure 3H:
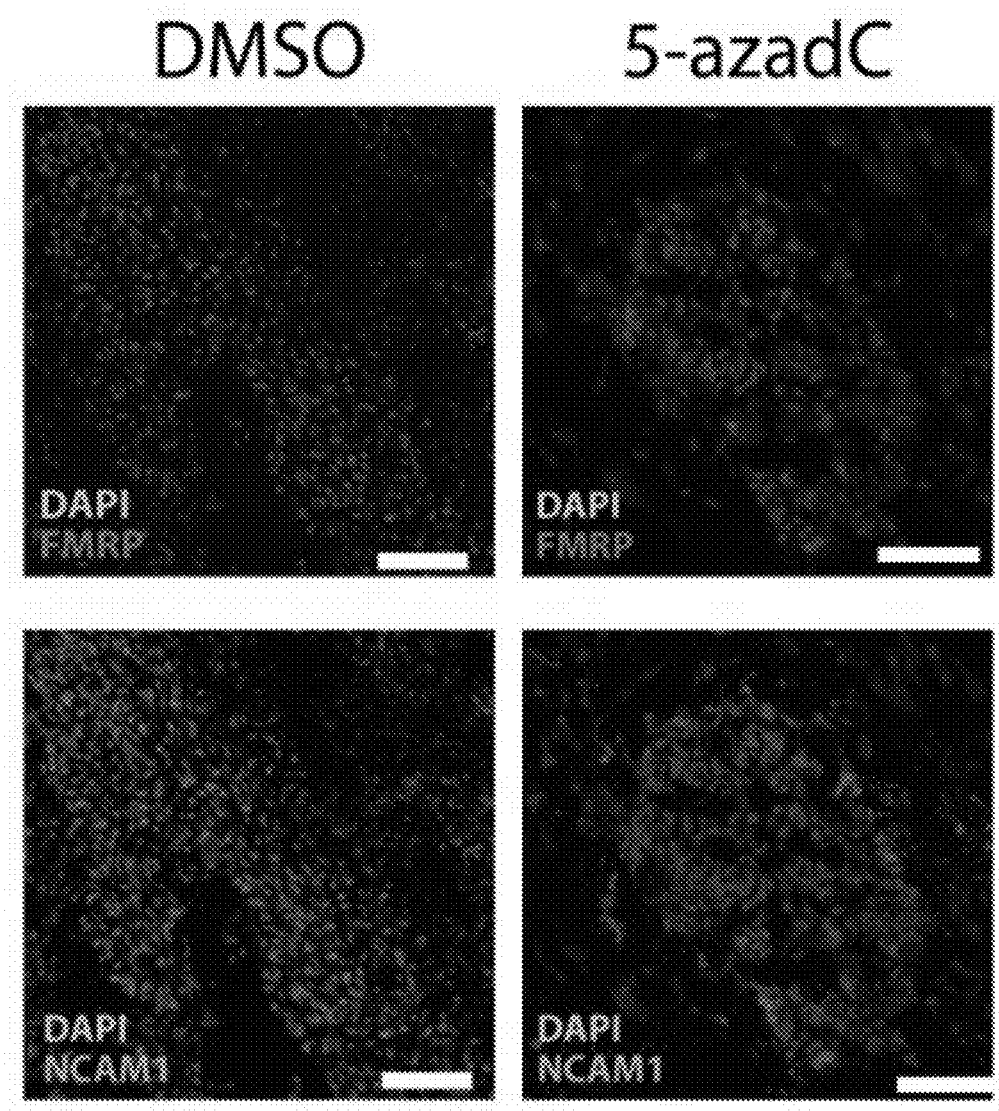
Figure 3J:
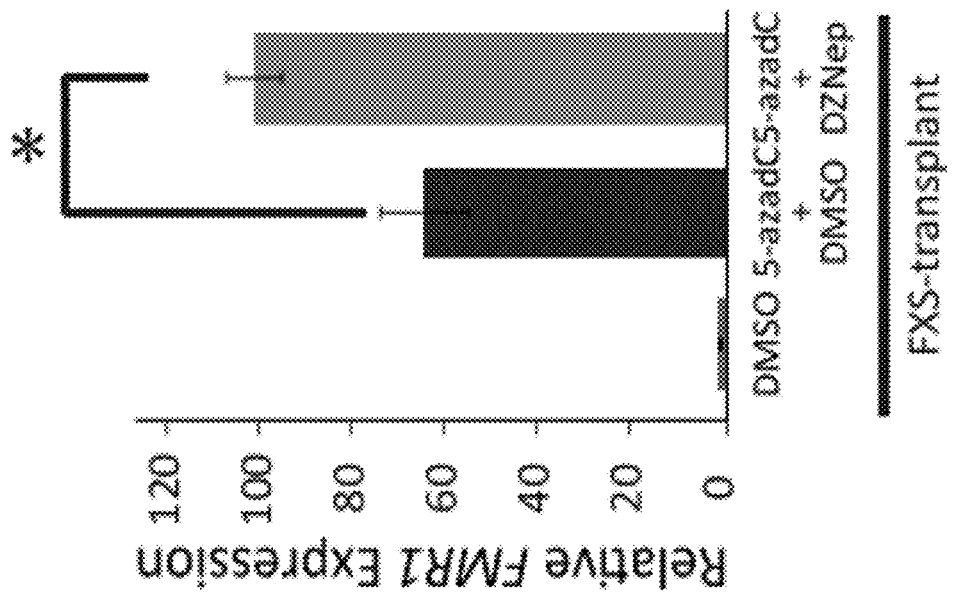
Figure 3I:
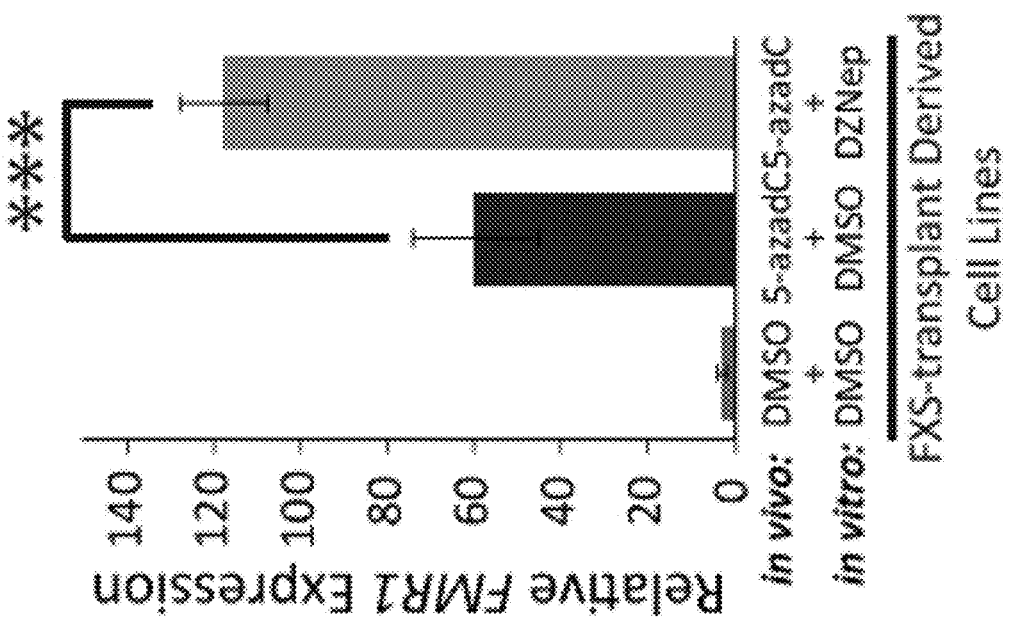
Figure 3K:
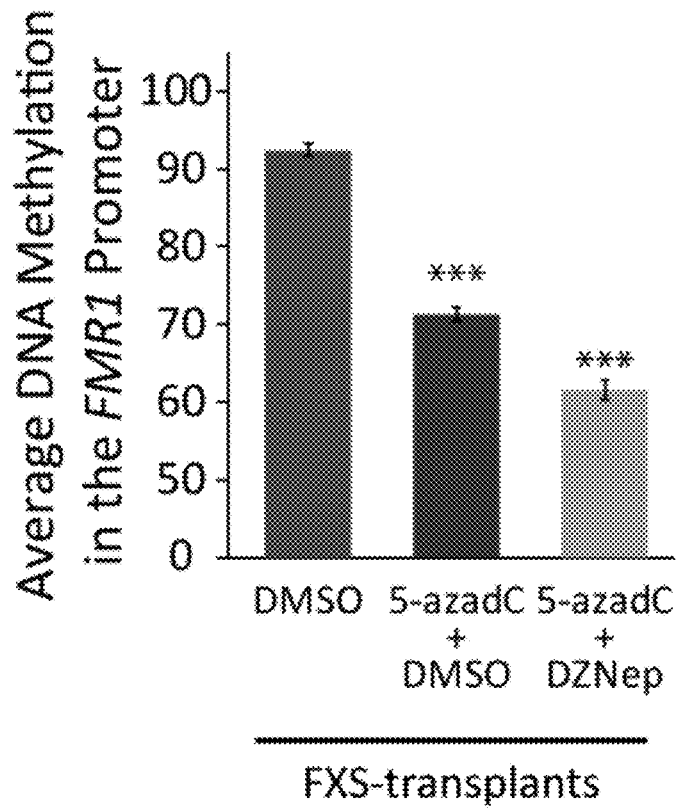
Figure 3L:
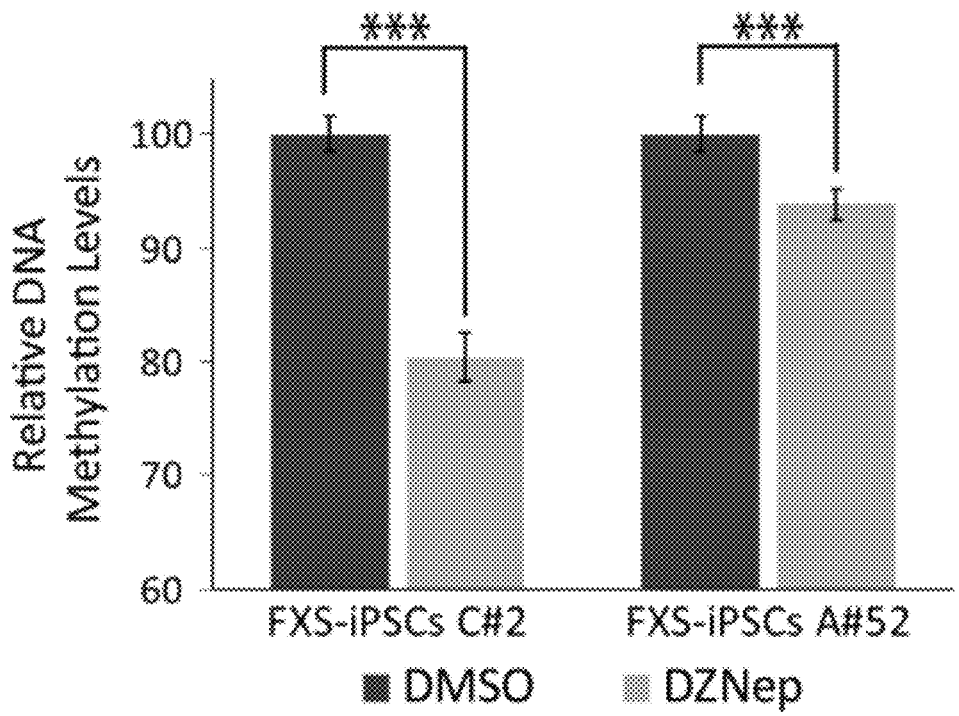
Figure 3M:
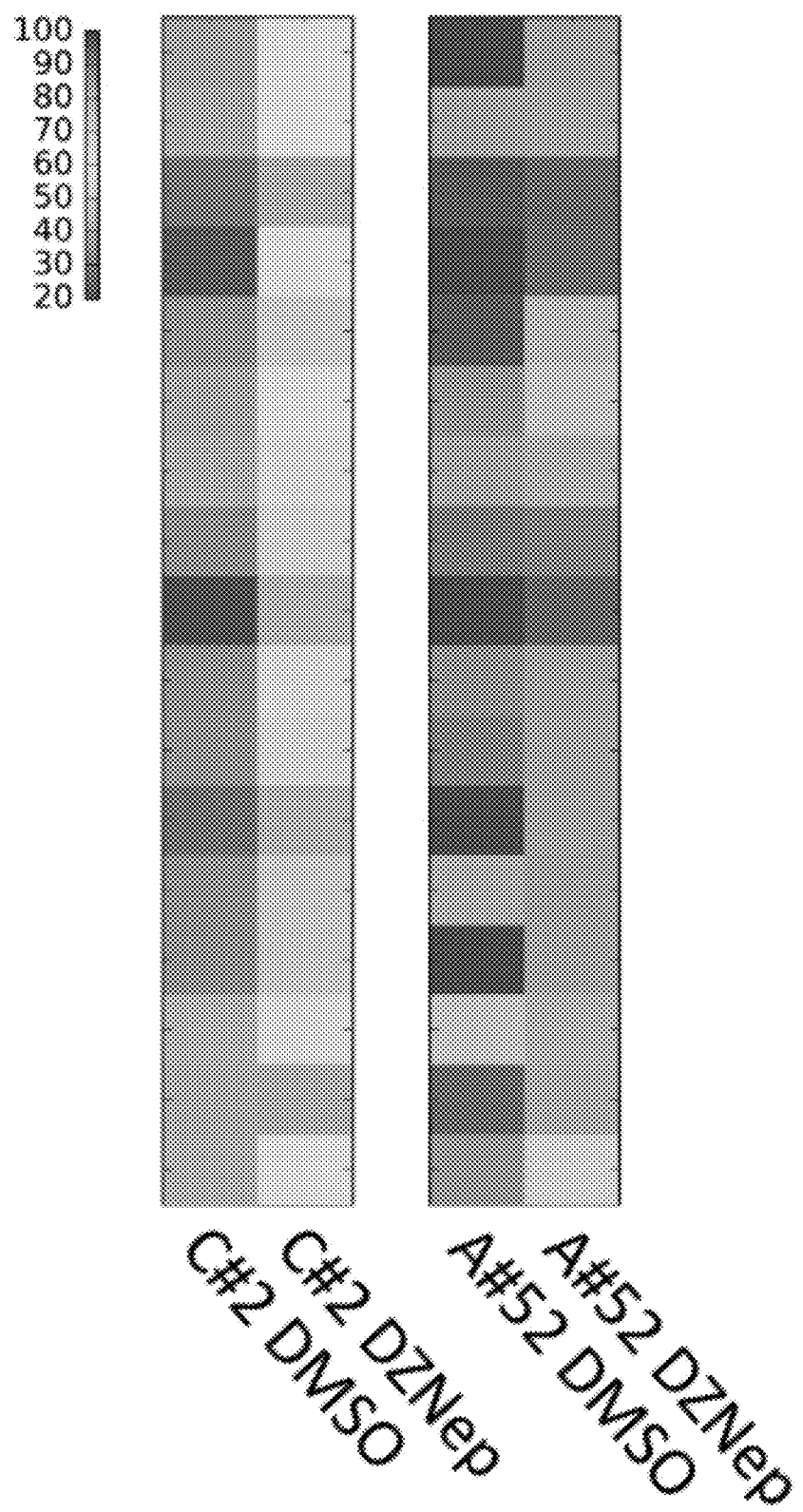

One of the hallmark features of human PSCs is their ability to undergo spontaneous differentiation upon implantation into an immune-compromised mouse, forming a differentiated tissue comprised of cells from all embryonic germ layers, including neural structures. We aimed to utilize this capability to test the in vivo efficacy of FMR1 reactivating treatments in the context of a heterogeneous tissue, upon systemic administration. We therefore generated FXS-differentiated transplants by injecting FXS-iPSCs into NOD-SCID Il2rg$^{-/-}$ immunodeficient mice (FIG. 3A-B). 5 weeks post-transplant initiation, mice were treated with 5 intraperitoneal injections of 15 mg/kg/day 5-azadC (FIG. 3B). The systemic administration of 5-azadC was able to efficiently demethylate the FMR1 promoter (FIG. 3C) and to robustly induce FMR1 expression, both at the RNA (FIG. 3D-F) and protein levels (FIG. 3G-H). The expression of FMR1 mRNA continued to increase during the first 6 days following treatment withdrawal and remained stable for at least 30 days from the end of the treatment, without re-silencing of FMR1 expression or regaining of DNA hypermethylation in the FMR1 promoter (FIG. 3C-D). FMRP immunostaining demonstrated the localization of FMRP expression to primitive neural structures within the transplant (FIG. 3G-H). Next, we assessed the ability of DZNep treatment to potentiate the effects of 5-azadC mediated demethylation in vivo. As an attempt to isolate a homogenous population of differentiated cells, 5-azadC or DMSO treated transplants were manually dissociated and cultured with either DMSO or DZNep for 4 days. In 5-azadC treated FXS transplants, subsequent in vitro treatment with DZNep induced higher levels of FMR1 mRNA (FIG. 3I). Finally, we turned to test the combined treatment in vivo. 5-azadC treatment (5 mg/kg/day) was combined with either DZNep (20 mg/kg/day) or DMSO. Combined treatment with 5-azadC and DZNep resulted in higher FMR1 expression within FXS affected transplants than treatment with 5-azadC alone (FIG. 3J), as well as lower DNA methylation levels in the FMR1 promoter (FIGS. 3C and 3K). The dose of 5-azadC could be lowered even to 1 mg/kg/day and when combined with DZNep still produced a comparable FMR1 reduction to that induced by 5'azadC alone at the higher concentration. Interestingly, DZNep treatment alone of FXS-iPSCs was also able to induce a small decrease in the DNA methylation levels of FMR1 promoter, possibly due to an indirect effect mediated by the targeting of inhibitory histone modifications (FIG. 3L-M).

Figure 4A:
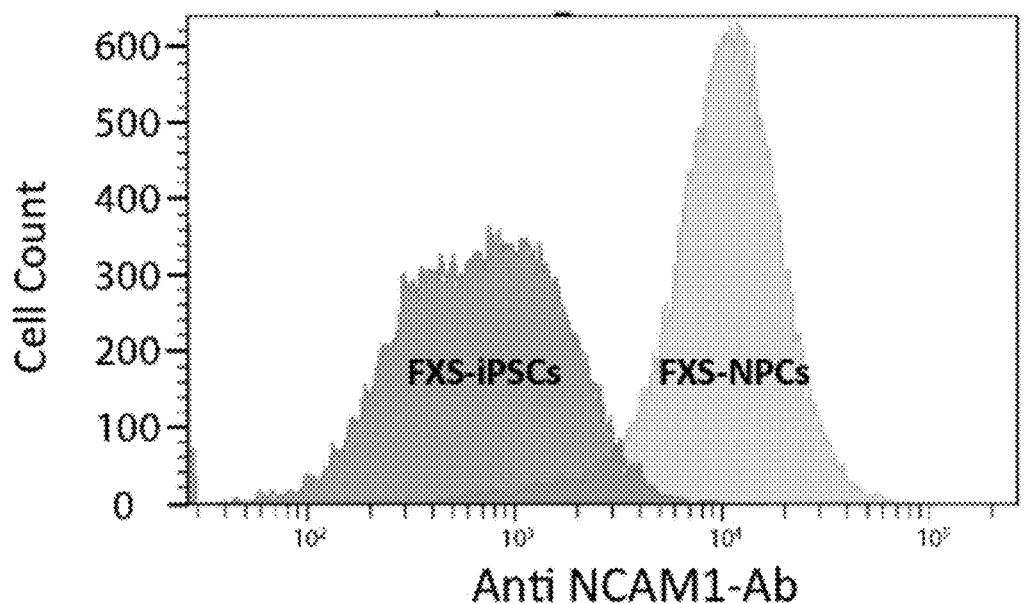
FIGS. 4A-K: FMR1 reactivation of human FXS-NPCs transplanted in murine brains. (4A) A histogram of anti-NCAM1 antibody sorting of FXS-iPSCs and FXS-NPCs. (4B) A bar graph of RT-PCR analysis of Pou5f1 and PAX6 expression in FXS-NPCs and FXS-iPSCs. (4C-D) Micrographs of detection of human neural precursor cells (NPCs) within murine brains. 12 days after human NPCs injection, murine brains were dissected and stained for human-specific anti mitochondria antibody (red). Human NPC grafts were detected upon injection into the (4C) lateral ventricles and (4D) hippocampus. (4E) Micrographs of immunofluorescent staining of FXS-NPCs grafts using anti-Nestin antibody. (4F) A bar graph of RT-PCR expression of human-specific GAPDH in FXS-affected NPC-grafts within murine brain following transplantation. While normal murine brain tissue does not show traces of GAPDH expression, FXS-NPCs and edited FXS-NPCs grafted tissues express the human GAPDH mRNA. Ct=Threshold Cycle. (4G) A bar graph showing systemic 5-azadC treatment reactivated FMR1 mRNA expression in FXS-NPC grafts, as measured by RT-PCR analysis with human specific FMR1 primers. (4H-K) Micrographs demonstrating (4I and 4K) the identification of human grafts within the murine brain (green), and (4H and 4J) human FMRP expression in 5-azadC treated grafts using human-specific anti-FMRP antibody (red). Cell nuclei were visualized using DAPI. LV=lateral ventricle. DG=dentate gyrus. CA1=cornu ammonis 1. Scale Bars: C-D=200 μm, E, H-K: left panel=200 μm, right panel=20 μm. *$p<0.05$, ***$p<0.001$. Error bars represent SEM.
Figure 4B:
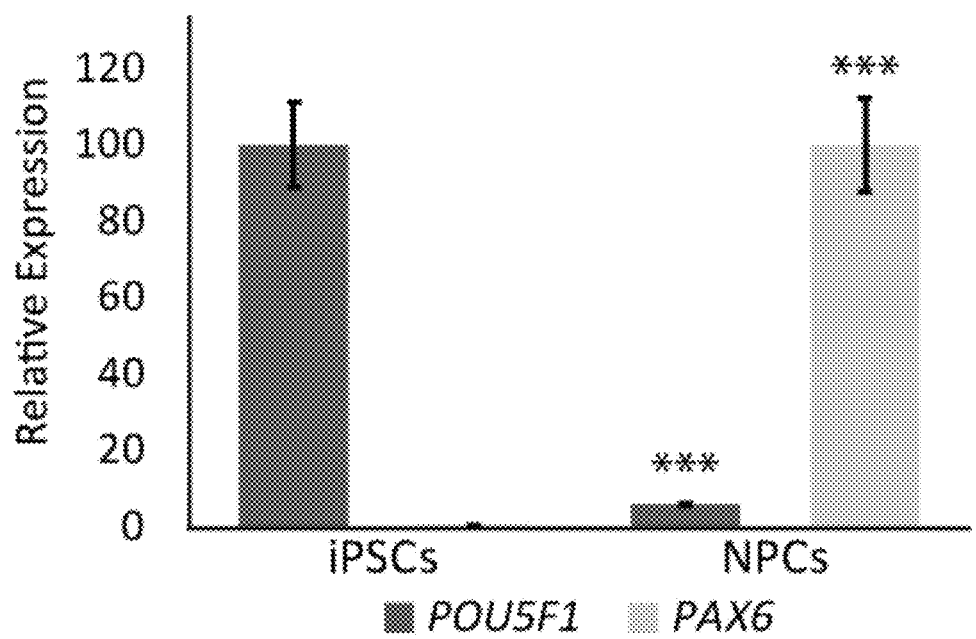
Figure 4C:
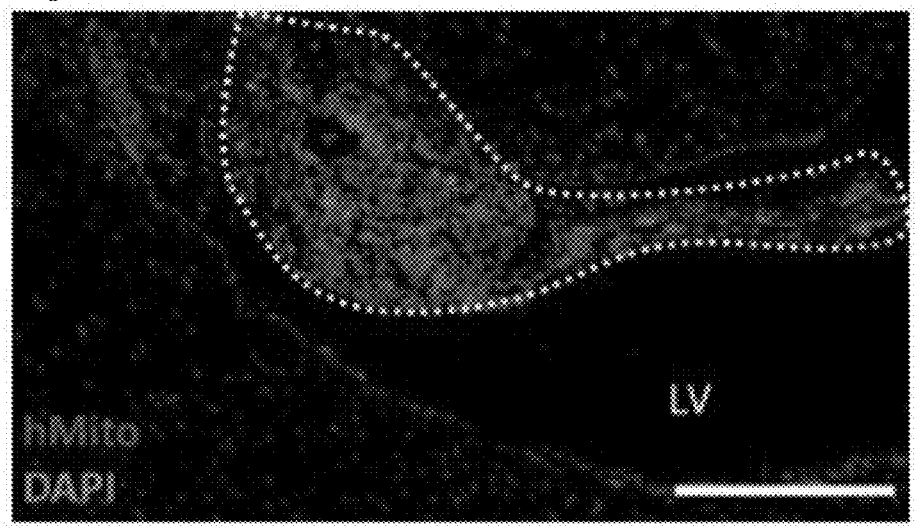
Figure 4D:
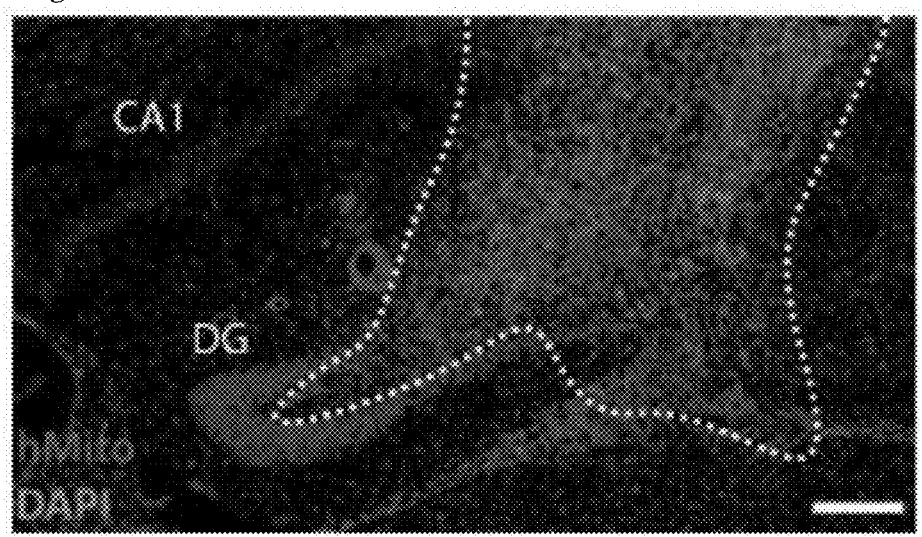
Figure 4E:
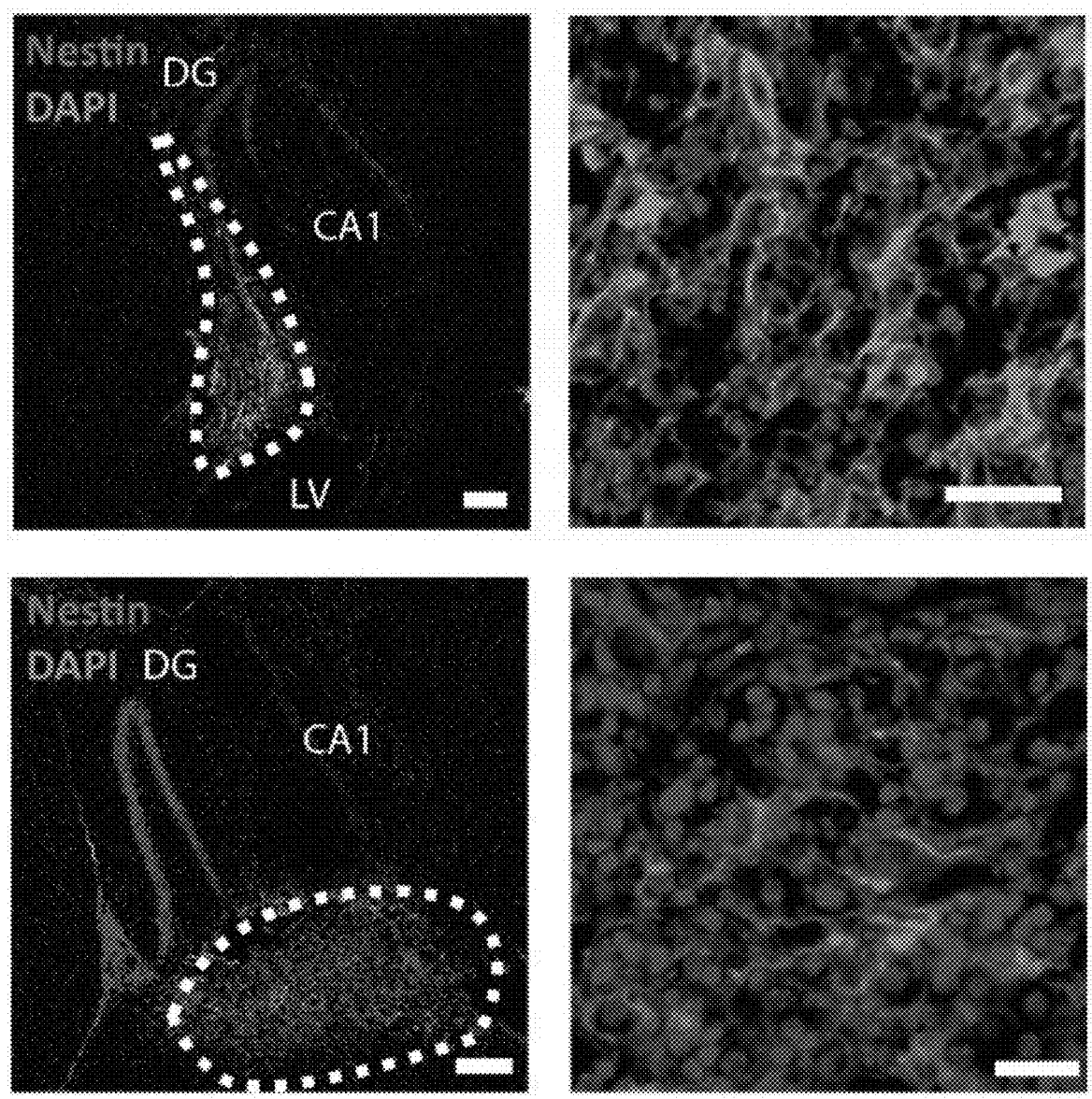

Example 6: FMR1 Reactivation in Human FXS-Neural Cells Transplanted in Rodent Brains Finally, as the main goal of a targeted treatment for FXS would be to alleviate the neurocognitive manifestations associated with this disorder, we established a for the evaluation of reactivating treatments in the context of the central nervous system (CNS). For this aim, FXS or corrected-FXS iPSCs were differentiated into NPCs (FIG. 4A-B) and injected into mouse brains. Three days following transplantation, the mice received daily intraperitoneal injections of 5-azadC or DMSO for 5 days. 3 days following the treatment the mice were sacrificed for histopathological analysis of the graft or RNA extraction. The transplanted human NPCs were identified in brain sections by immunofluorescent staining with human-specific anti-mitochondrial antibody, demonstrating the survival of human grafts within the murine brain (FIG. 4C-D). Transplanted NPC grafts were positively stained for Nestin, a protein marker for neural stem cells (FIG. 4E). The specificity of the monoclonal FMRP antibody towards human FMRP allowed the detection of FMRP reactivation within the human graft, without a contamination of mouse FMRP expressed in the murine brain.

Figure 4F:
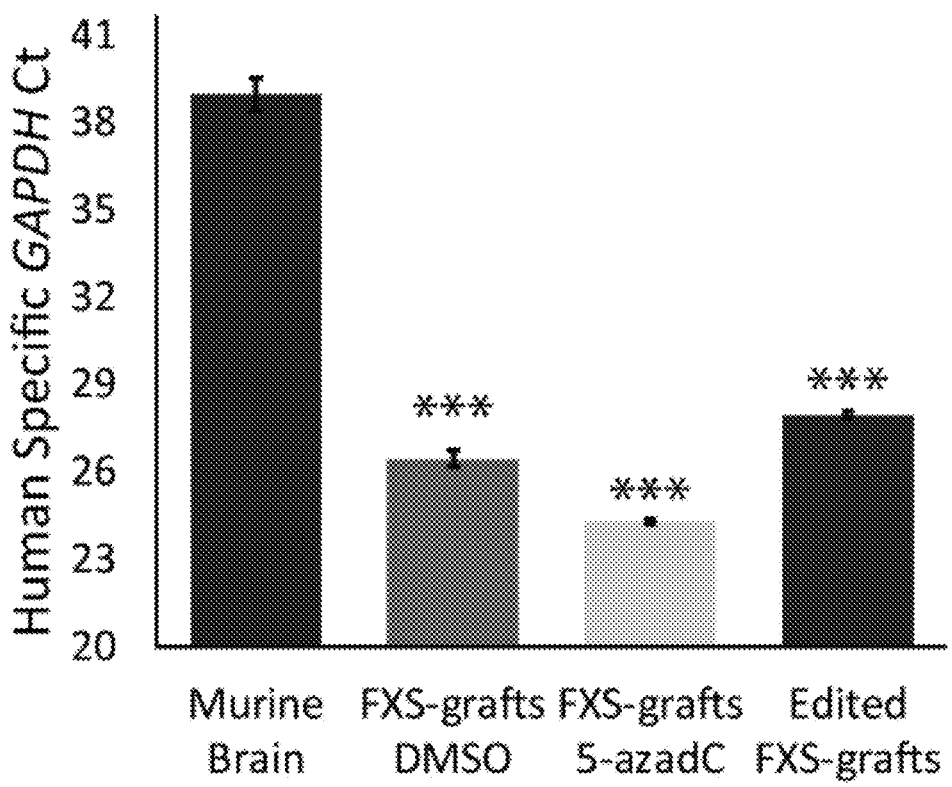
Figure 4G:
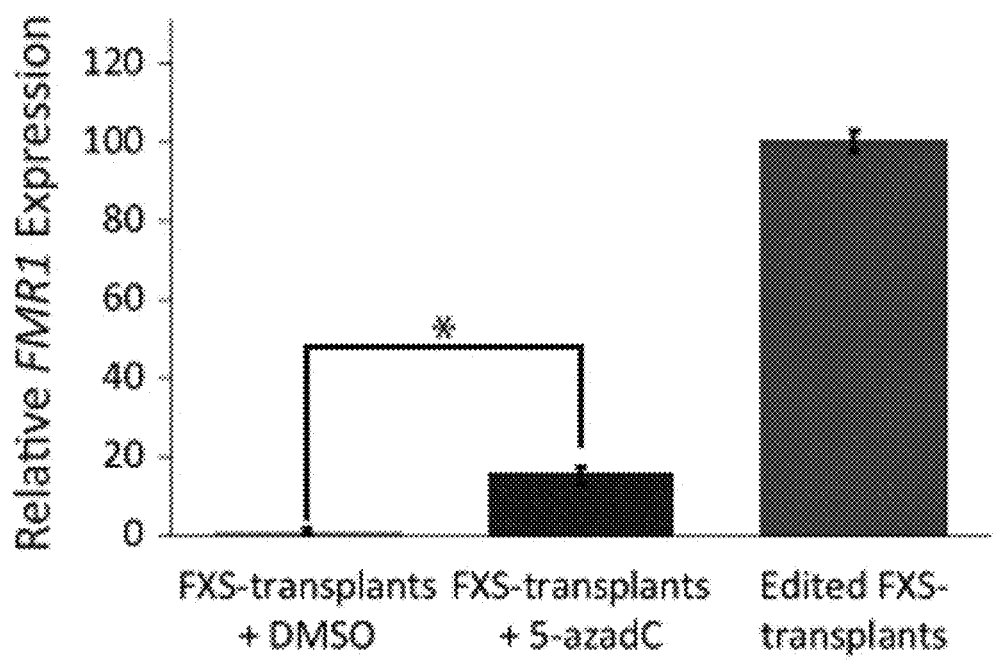
Figure 4I:
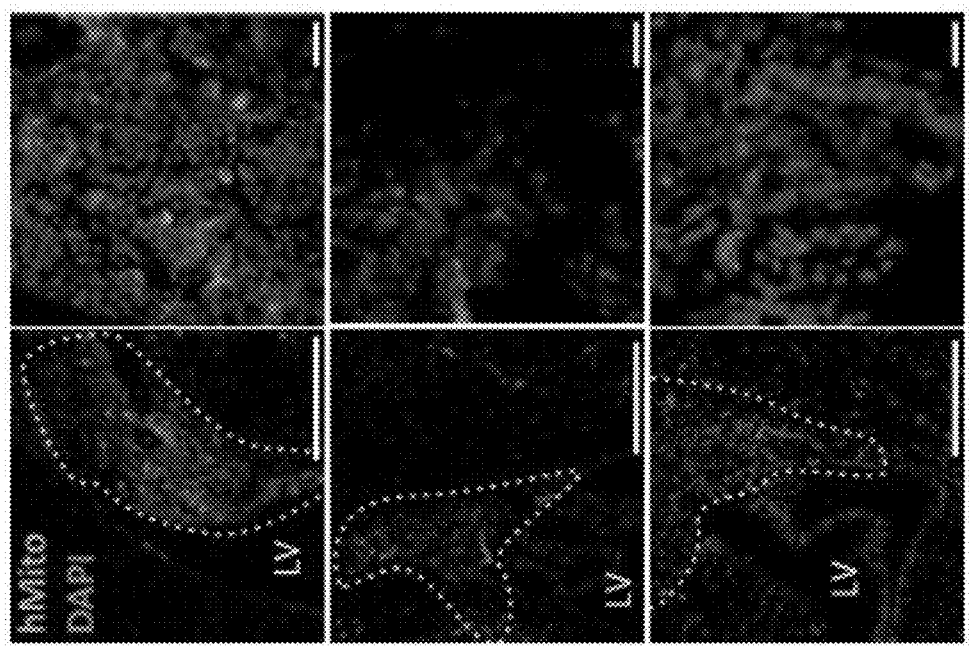
Figure 4H:
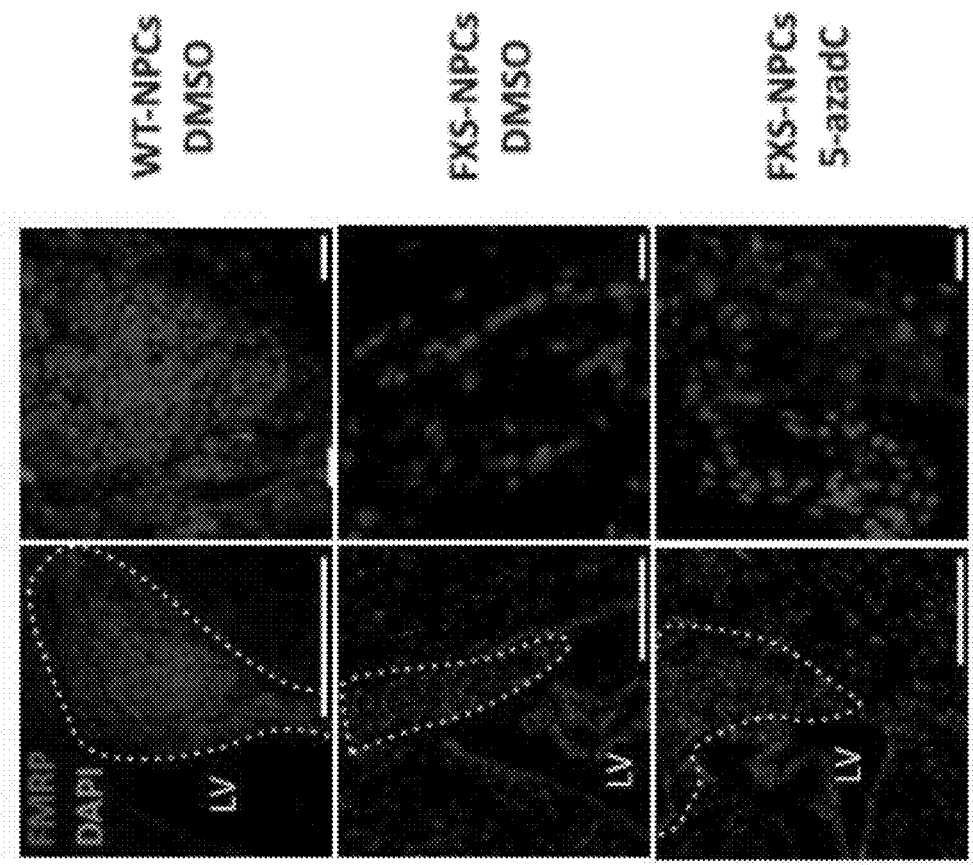
Figure 4K:
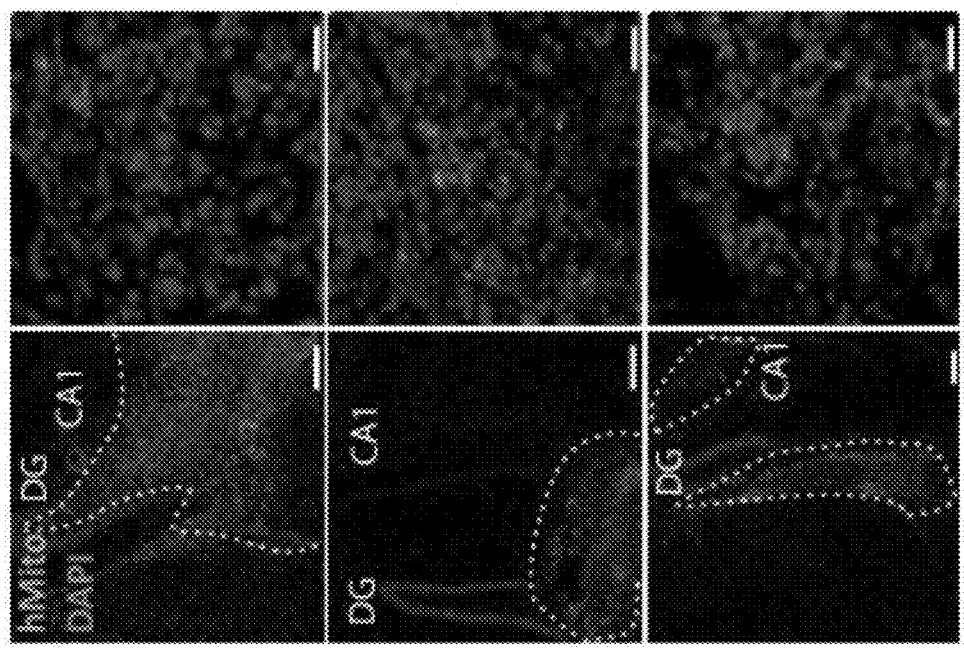
Figure 4J:
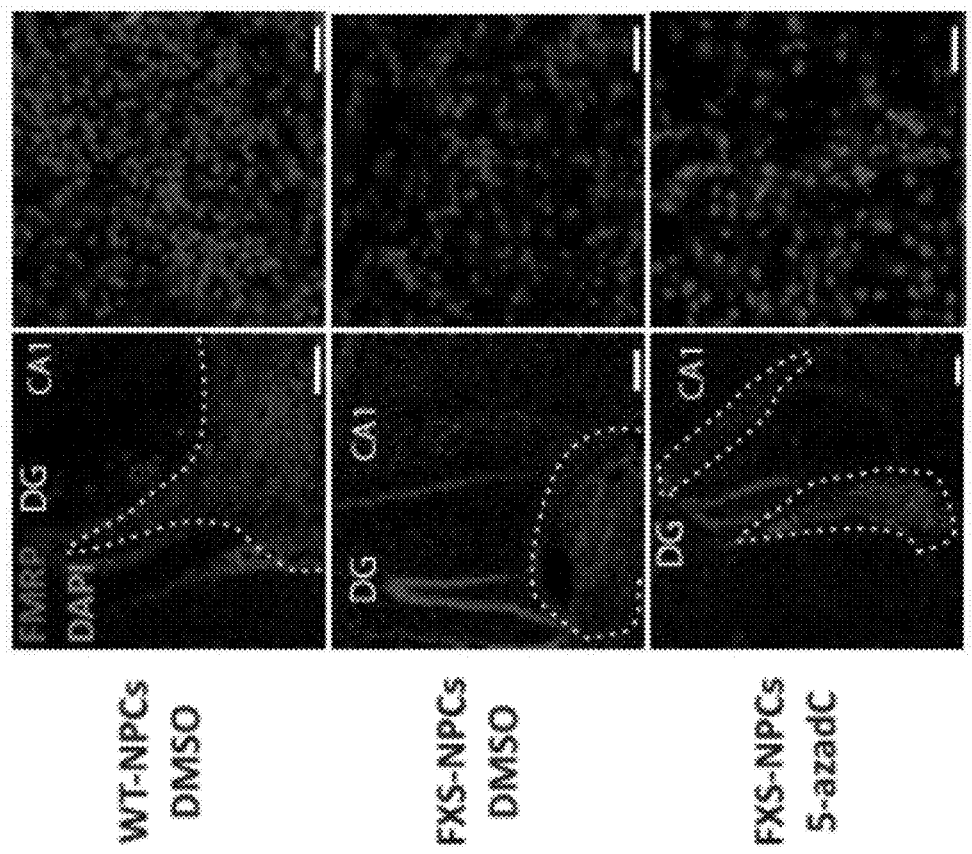

For RNA extraction, treated and untreated brains were excised and the grafts inside the target structures were dissected. Quantitative RT-PCR analysis of human-specific primers for the GAPDH gene mRNA confirmed the existence of human GAPDH mRNA only in grafted regions, but not in normal murine brain structures (FIG. 4F). Next, human specific primers for the FMR1 mRNA were used to demonstrate the complete silencing of FMR1 in FXS-affected grafts, as well as the restoration of FMR1 mRNA in the 5-azadC treated grafts (FIG. 4G). Finally, Immunofluorescence staining of the mouse brain sections showed FMRP reactivation in 5-azadC treated human FXS-NPC grafts, demonstrating the feasibility of FMR1 transcriptional therapy within the central nervous system (FIG. 4H-K).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of reactivating transcription of a fragile X mental retardation 1 (FMR1) gene in a cell, comprising contacting said cell with 5-aza-2-deoxycytidine (5-azadC) and 3-Deazaneoplanocin A (DZNep), thereby reactivating transcription of said FMR1 gene in said cell.

2. A method of treating an FMR1-associated disease in a subject in need thereof, the method comprising administering to said subject 3-Deazaneoplanocin A (DZNep) in combination with 5-aza-2-deoxycytidine (5-azadC), thereby treating an FMR1-associated disease in a subject.

3. The method of claim 1, wherein said cell comprises an expansion of a repetitive CGG sequence in a 5' UTR of a FMR1 gene.

4. The method of claim 3, wherein said expansion comprises at least 55 CGG repeats.

5. The method of claim 3, wherein said expansion comprises at least 200 repeats.

6. The method of claim 1, wherein said cell is a neuronal cell.

7. The method of claim 6, wherein said neuronal cell is from a region of the brain selected from hippocampus, temporal cortices, visual cortex, cerebral cortex, amygdala, caudate nucleus, and temporal gyrus.

8. The method of claim 7, wherein said neuronal cell is located in the hippocampus.

9. The method of claim 2, wherein said 5-azadC and DZNep are administered simultaneously or sequentially.

10. The method of claim 9, wherein said 5-azadC and DZNep are administered simultaneously.

11. The method of claim 9, wherein said 5-azadC and DZNep are administered less than 3 days apart.

12. The method of claim 2, wherein said treating comprises reactivation of transcription of FMR1.

13. The method of claim 1, wherein said reactivating persists for longer than 30 days.

14. The method of claim 1, wherein said reactivating comprises increased expression of FMR1 as compared to reactivation with 5-azadC alone, and wherein said increase occurs within 3 days of said contacting or administering.

15. The method of claim 14, wherein said increased expression comprises an increase of at least 30% by 4 days after said contacting or administering.

16. The method of claim 2, wherein said administering comprises intravenous, intracranial, or intrathecal administration.

17. The method of claim 2, wherein said administering comprises a 5-azadC dosage of between 0.1 and 2 mg/kg/day.

18. The method of claim 2, wherein said FMR1-associated disease is selected from Fragile X Syndrome (FXS), schizophrenia, bipolar disorder, psychotic bipolar disorder, dementia, fragile X-associated tremor/ataxia syndrome (FX-TAS), and FMR1-related primary ovarian insufficiency (POI), Angelman syndrome, Prader-Willi Syndrome, Beckwith-Wiedemann syndrome, Silver-Russell syndrome, lupus, rheumatoid arthritis, multiple sclerosis, diabetes and alcoholism.

19. The method of claim 18, wherein said FMR1-associated disease is FXS.

* * * * *